United States Patent
Takahashi et al.

(10) Patent No.: US 9,632,061 B2
(45) Date of Patent: Apr. 25, 2017

(54) EDDY CURRENT SENSOR AND POLISHING METHOD

(71) Applicant: Ebara Corporation, Tokyo (JP)

(72) Inventors: Taro Takahashi, Tokyo (JP); Mitsuo Tada, Tokyo (JP)

(73) Assignee: Ebara Corporation, Tokyo (JP)

(*) Notice: Subject to any disclaimer, the term of this patent is extended or adjusted under 35 U.S.C. 154(b) by 653 days.

(21) Appl. No.: 13/853,023

(22) Filed: Mar. 28, 2013

(65) Prior Publication Data

US 2013/0260645 A1    Oct. 3, 2013

(30) Foreign Application Priority Data

Mar. 30, 2012 (JP) .................................. 2012-79555

(51) Int. Cl.
| | | |
|---|---|---|
| *G01N 27/82* | (2006.01) | |
| *G01N 27/90* | (2006.01) | |
| *B24B 49/10* | (2006.01) | |
| *B24B 37/013* | (2012.01) | |
| *H01L 21/66* | (2006.01) | |

(52) U.S. Cl.
CPC ........... *G01N 27/90* (2013.01); *B24B 37/013* (2013.01); *B24B 49/105* (2013.01); *G01N 27/82* (2013.01); *H01L 22/14* (2013.01); *H01L 22/26* (2013.01); *H01L 2924/0002* (2013.01)

(58) Field of Classification Search
CPC ........... G01B 7/105; G01B 7/06; G01N 27/82
USPC ................................................. 324/240, 228
See application file for complete search history.

(56) References Cited

U.S. PATENT DOCUMENTS

| | | | | |
|---|---|---|---|---|
| 3,986,105 A | * | 10/1976 | Nix ........................ | G01B 7/105 324/230 |
| 6,310,476 B1 | * | 10/2001 | Kawanami ......... | G01N 27/9053 324/225 |
| 8,454,407 B2 | * | 6/2013 | Takahashi ............. | B24B 49/105 451/5 |
| 2011/0124269 A1 | | 5/2011 | Tada et al. | |

FOREIGN PATENT DOCUMENTS

| | | |
|---|---|---|
| JP | 10-111279 A | 4/1998 |
| JP | 2011-23579 A | 2/2011 |

* cited by examiner

*Primary Examiner* — Reena Aurora
(74) *Attorney, Agent, or Firm* — Baker & Hostetler LLP

(57) ABSTRACT

An eddy current sensor is used for detecting a metal film (or conductive film) formed on a surface of a substrate such as a semiconductor wafer. The eddy current sensor is disposed near the metal film or the conductive film formed on the substrate to detect an eddy current generated in the metal film or the conductive film. The eddy current sensor includes a plurality of coils having different sizes formed by winding a wire or a conductive material. The plurality of coils includes an inner coil and an outer coil spaced from each other, and the outer coil is configured to surround the inner coil. The plurality of coils are configured to detect respective eddy currents generated in the metal film or the conductive film.

20 Claims, 25 Drawing Sheets five rows and two layers (ten turns)

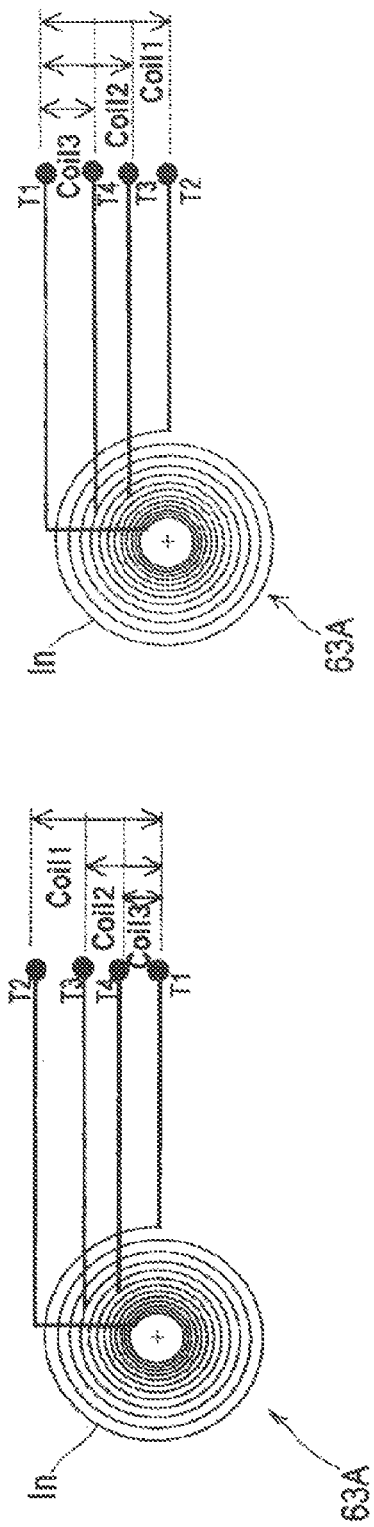

FIG. 20A
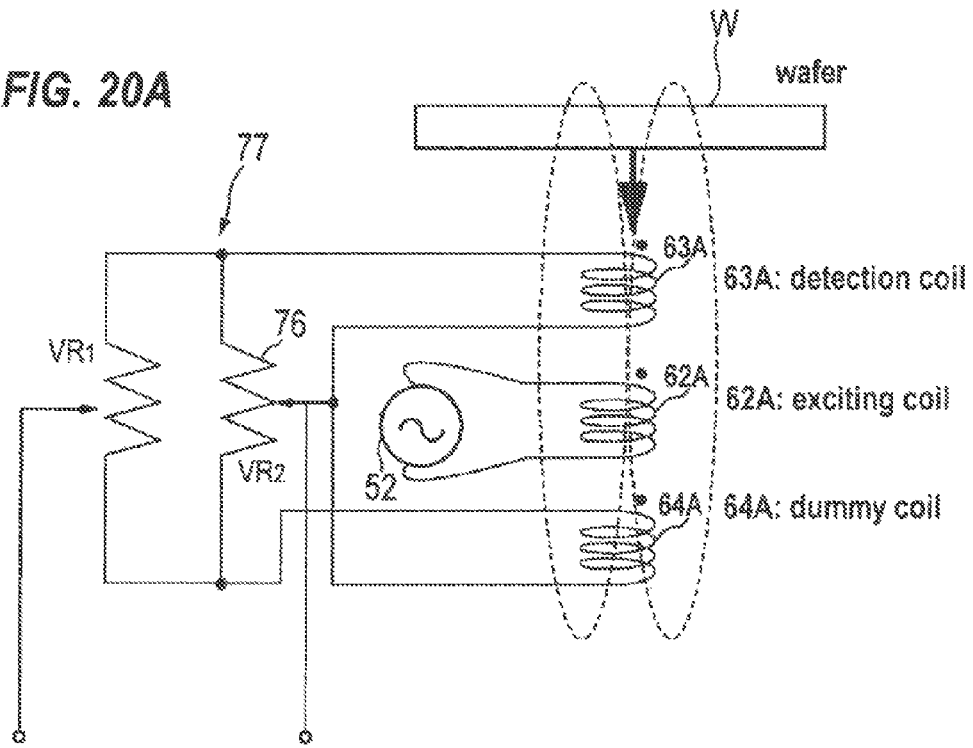
FIG. 20B
FIG. 20C
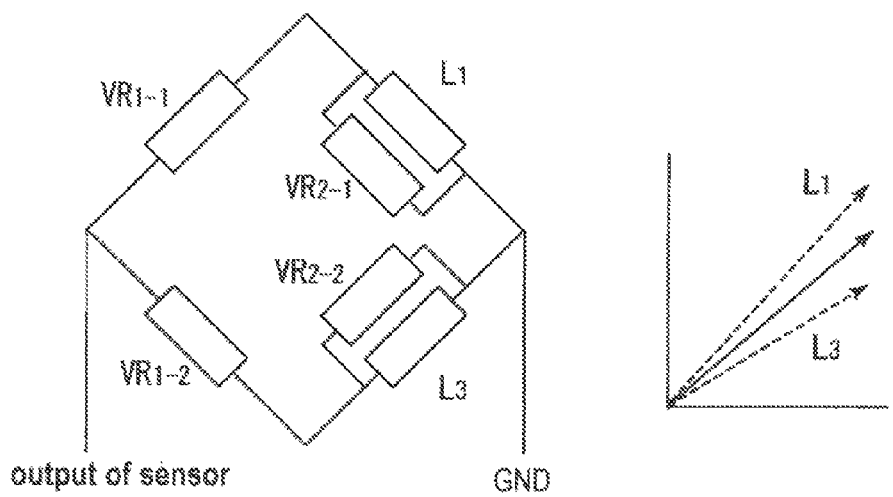

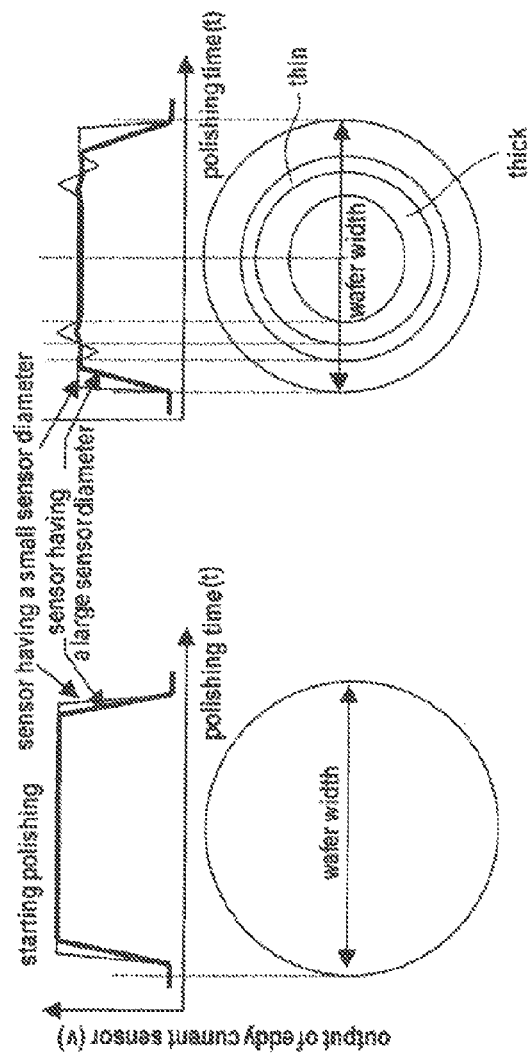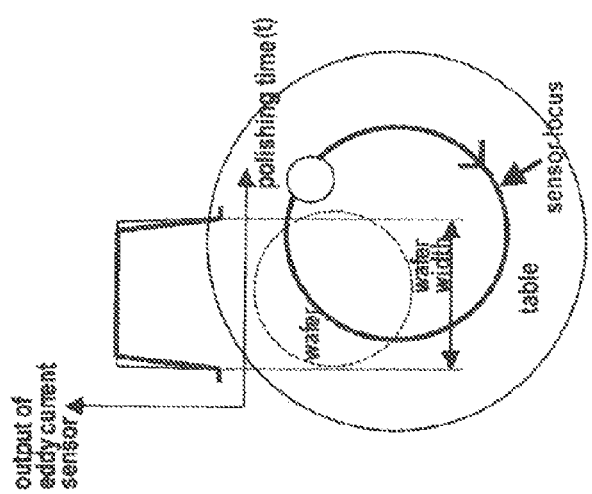

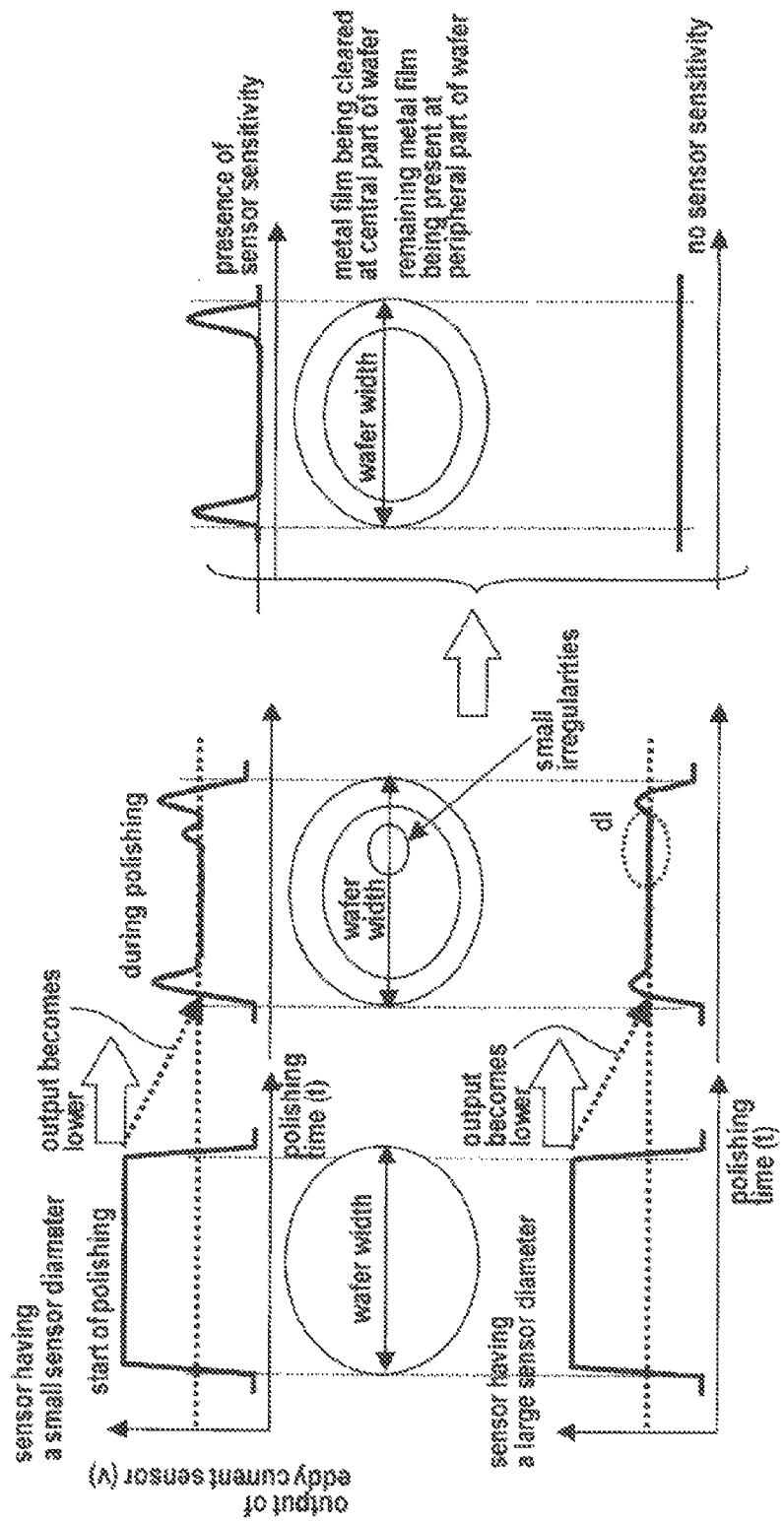

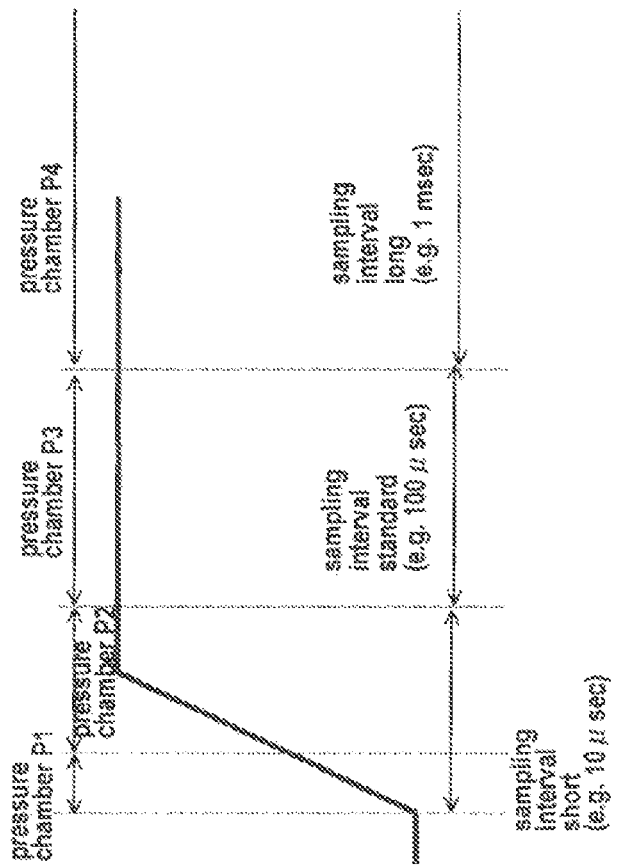
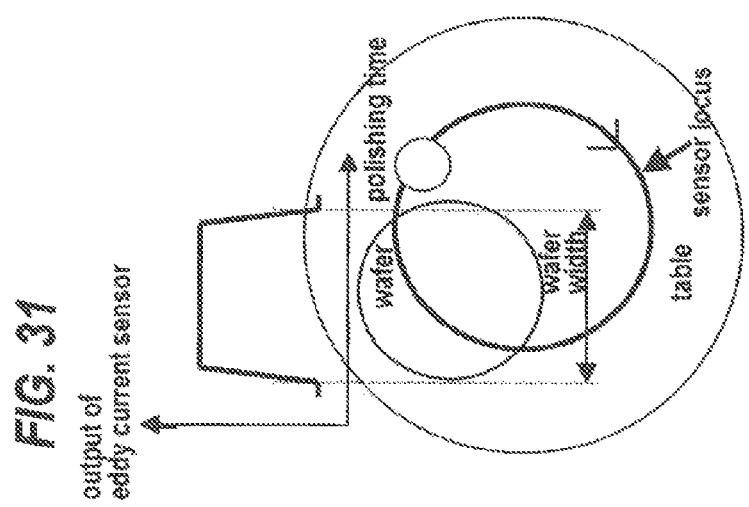
FIG. 31

EDDY CURRENT SENSOR AND POLISHING METHOD

CROSS REFERENCE TO RELATED APPLICATIONS

This document claims priority to Japanese Application Number 2012-079555, filed Mar. 30, 2012, the entire contents of which are hereby incorporated by reference.

BACKGROUND OF THE INVENTION

Field of the Invention

The present invention relates to an eddy current sensor suitable for detecting a metal film (or conductive film) formed on a surface of a substrate such as a semiconductor wafer. Further, the present invention relates to a polishing method and apparatus for polishing the substrate while monitoring the metal film (or conductive film) formed on the substrate by the eddy current sensor to remove the metal film (or conductive film).

Description of the Related Art

In recent years, high integration and high density in semiconductor device demands smaller and smaller wiring patterns or interconnections and also more and more interconnection layers. Multilayer interconnections in smaller circuits result in greater steps which reflect surface irregularities on lower interconnection layers. An increase in the number of interconnection layers makes film coating performance (step coverage) poor over stepped configurations of thin films. Therefore, better multilayer interconnections need to have the improved step coverage and proper surface planarization. Further, since the depth of focus of a photolithographic optical system is smaller with miniaturization of a photolithographic process, a surface of the semiconductor device needs to be planarized such that irregular steps on the surface of the semiconductor device will fall within the depth of focus.

Thus, in a manufacturing process of a semiconductor device, it increasingly becomes important to planarize a surface of the semiconductor device. One of the most important planarizing technologies is chemical mechanical polishing (CMP). In the chemical mechanical polishing, while a polishing liquid containing abrasive particles such as silica ($SiO_2$) therein is supplied onto a polishing surface such as a polishing pad, a substrate such as a semiconductor wafer is brought into sliding contact with the polishing surface and polished using the polishing apparatus.

In forming the above mentioned multilayer interconnections, there has been performed a process in which grooves for interconnections having a predetermined pattern are formed in an insulating layer (dielectric material) on a substrate, the substrate is then dipped in a plating solution to plate the substrate with copper (Cu), for example, by an electroless plating or an electrolytic plating, and then unnecessary portions of a copper layer is selectively removed from the substrate by a CMP process, while leaving only the copper layer in the grooves for interconnections. In this case, if the substrate is insufficiently polished to leave the copper layer on the insulating layer (oxide film), then the circuits would not be separated from each other, but short-circuited. Conversely, if the copper layer in the interconnection grooves is excessively polished away together with the insulating layer, then the resistance of the circuits on the substrate would be so increased that the entirety of the semiconductor substrate might possibly need to be discarded, resulting in a large loss. This holds true for the cases in which other metal films such as aluminum layer are formed, and then polished by the CMP process.

The polishing apparatus which performs the above-mentioned CMP process includes a polishing table having a polishing surface formed by a polishing pad, and a substrate holding device, which is referred to as a top ring or a polishing head, for holding a semiconductor wafer (substrate). When a semiconductor wafer is polished with such a polishing apparatus, the semiconductor wafer is held and pressed against the polishing surface under a predetermined pressure by the substrate holding device so that the metal film on the semiconductor wafer is removed.

After a polishing process is completed, if a subsequent process is carried out in such a state that the metal film is left on the semiconductor wafer, then problems of short circuit or the like occur, and thus the semiconductor wafer cannot be used. Therefore, after the polishing process is completed, the wafer is separated and moved away from the polishing pad (polishing surface), and then an inspection on the presence of the remaining metal film is carried out. In this manner, although it is possible to confirm the remaining film, it takes time for inspection to reduce wafer processing capability. After the inspection, if the remaining film is detected on the wafer, then it is necessary to carry out repolishing. However, in the case where polishing is carried out after the wafer is moved away from the polishing pad, processing time per wafer increases. That is, the throughput is lowered.

In order to solve the above problem of lowering of the throughput caused by the inspection on the presence of the remaining metal film and the repolishing after the inspection, in Japanese laid-open patent publication No. 2011-23579, there has been proposed a polishing method and apparatus which can shorten inspection time by performing an inspection on whether or not there is a remaining film of a metal film (or conductive film) on a substrate such as a semiconductor wafer during polishing, and can shorten processing time by performing additional polishing of the substrate as it is in the case where the remaining film is detected.

SUMMARY OF THE INVENTION

In the proposed Japanese laid-open patent publication No. 2011-23579, an eddy current sensor which responds to a metal film such as a Cu film formed on a substrate such as a semiconductor wafer is disposed in a polishing table and the eddy current sensor outputs a certain voltage value in response to the metal film of the substrate while the eddy current sensor passes through under the substrate by rotation of the polishing table during polishing of the substrate, and thus removal of the metal film is detected by monitoring the output of the eddy current sensor. In this case, detection of the thin metal film when polishing progresses is performed by increasing oscillation frequency of the eddy current sensor, increasing amplification degree of an internal circuit of the eddy current sensor, or increasing exciting voltage of the eddy current sensor.

Also, in the case where there is another material metal film under the metal film which is being polished and another material metal film (or conductive film) is detected in the progress of the polishing, the detection is performed in the same way, i.e., by changing the sensitivity of the sensor, such as by increasing oscillation frequency of the eddy current sensor.

The oscillation frequency of the eddy current sensor is needed to be set lower than a coil resonance frequency which is determined by inductance and capacitance of the coil itself. In the case where the oscillation frequency is set around the coil resonance frequency, there is a problem of stability of characteristics. Further, in the case where the amplification degree of the internal circuit of the eddy current sensor is increased, influence of a circuit noise becomes greater. Further, in the case where the exciting voltage of the eddy current sensor is increased, there is a problem of stability of characteristics.

To detect the material or thickness of the different film, besides change of the sensitivity of the sensor, a plurality of sensors which have different sensitivity or differ in type are disposed at different locations in the polishing table.

However, in the case where a plurality of sensors are disposed at different locations, loci along which the sensors pass through under the substrate differ from one another, and thus the plurality of sensors detect the film at different locations of the surface, being polished, of the substrate. Therefore, it is difficult to estimate the film thickness accurately along the same locus.

The present invention has been made in view of the above circumstances. It is therefore an object of the present invention to provide an eddy current sensor which is capable of detecting accurately a thin metal film (or thin conductive film) on a substrate such as a semiconductor wafer without increasing oscillation frequency, amplification degree of an internal circuit and exciting voltage of the eddy current sensor, and without disposing a plurality of sensors which have different sensitivity at different locations in the polishing table.

Further, it is an object of the present invention to provide a polishing method and apparatus which can shorten inspection time by performing an inspection using an eddy current sensor on whether or not there is a remaining film of a metal film (or conductive film) on a substrate during polishing, and can shorten processing time by performing additional polishing of the substrate as it is in the case where the remaining film is detected.

In order to achieve the above object, according to a first aspect of the present invention, there is provided an eddy current sensor disposed near a metal film or a conductive film formed on a substrate to detect an eddy current generated in the metal film or the conductive film, the eddy current sensor comprising: a plurality of coils having different sizes formed by winding a wire or a conductive material, the plurality of coils comprising an inner coil and an outer coil spaced from each other, the outer coil being configured to surround the inner coil; wherein the plurality of coils are configured to detect respective eddy currents generated in the metal film or the conductive film.

According to a second aspect of the present invention, there is provided an eddy current sensor disposed near a metal film or a conductive film formed on a substrate to detect an eddy current generated in the metal film or the conductive film, the eddy current sensor comprising: a plurality of coils arranged one above the other in a direction perpendicular to the substrate, the plurality of coils having different sizes formed by winding a wire or a conductive material; wherein the plurality of coils are configured to detect respective eddy currents generated in the metal film or the conductive film.

According to the first and second aspects of the present invention, since the plurality of coils for detecting the eddy current in the eddy current sensor comprise a coil having a small size and a coil having a large size, the plurality of coils can detect respective eddy currents generated in two or more areas which comprise a small area (first area) and a large area (second area) including the small area (first area) on the substrate. Therefore, the eddy currents detected respectively and simultaneously at two or more areas which have an overlapping area can be compared, and the metal film or the conductive film can be detected with high accuracy.

In a preferred aspect of the present invention, the plurality of coils comprise a coil having a small outer coil diameter and a coil having a large outer coil diameter, or a coil having a small median coil diameter and a coil having a large median coil diameter, the median coil diameter being defined as an arithmetic average of an inner diameter and an outer diameter of the coil.

In a preferred aspect of the present invention, a plurality of the coils having a small outer coil diameter are connected in series to form a serially connected coils having a small outer coil diameter, and a plurality of the coils having a large outer coil diameter are connected in series to form a serially connected coils having a large outer coil diameter, and one of the serially connected coils having a small outer coil diameter and the serially connected coils having a large outer coil diameter is located between the serially connected coils of the other.

In a preferred aspect of the present invention, a plurality of the coils having a small median coil diameter are connected in series to form a serially connected coils having a small median coil diameter, and a plurality of the coils having a large median coil diameter are connected in series to form a serially connected coils having a large median coil diameter, and one of the serially connected coils having a small median coil diameter and the serially connected coils having a large median coil diameter is located between the serially connected coils of the other.

In a preferred aspect of the present invention, the plurality of coils comprise a plurality of detection coils configured to detect the respective eddy currents generated in the metal film or the conductive film.

In a preferred aspect of the present invention, the eddy current sensor further comprises a plurality of exciting coils, each of the plurality of exciting coils being connected to an AC signal source and configured to generate an eddy current in the metal film or the conductive film, wherein the plurality of exciting coils comprise an inner exciting coil and an outer exciting coil spaced from each other, the outer exciting coil being configured to surround the inner exciting coil.

In a preferred aspect of the present invention, the eddy current sensor further comprises a plurality of exciting coils, each of the plurality of exciting coils being connected to an AC signal source and configured to generate an eddy current in the metal film or the conductive film, wherein the plurality of exciting coils are arranged one above the other in a direction perpendicular to the substrate.

According to the present invention, since the plurality of exciting coils in the eddy current sensor comprise a coil having a small size and a coil having a large size, the plurality of coils can generate respective eddy currents in two or more areas which comprise a small area (first area) and a large area (second area) including the small area (first area) on the substrate.

In a preferred aspect of the present invention, the eddy current sensor further comprises a plurality of dummy coils connected to the respective detection coils in series, wherein the plurality of dummy coils comprise an inner dummy coil and an outer dummy coil spaced from each other, the outer dummy coil being configured to surround the inner dummy coil.

In a preferred aspect of the present invention, the eddy current sensor further comprises a plurality of dummy coils connected to the respective detection coils in series, wherein the plurality of dummy coils are arranged one above the other in a direction perpendicular to the substrate.

In a preferred aspect of the present invention, at least one of the plurality of detection coils comprises a coil formed by winding the wire or the conductive material by a single row and plural layers, the row being defined as a direction perpendicular to the substrate and the layer being defined as a direction parallel to the substrate.

According to the eddy current sensor of the present invention, since at least one of the plurality of detection coils of the eddy current sensor comprises a coil formed by winding a wire or a conductive material in a single row and plural layers, the detection coil can be brought close to the substrate, and capacitance component between lines can be small, thus improving sensor sensitivity. Therefore, the thin metal film (or thin conductive film) on the substrate such as a semiconductor wafer can be detected without increasing oscillation frequency, amplification degree of an internal circuit and exciting voltage of the eddy current sensor. The detection coil may be flat so as to have a thickness corresponding to only a diameter of the wire or a conductive material in a row direction by winding the wire or the conductive material in a spiral fashion by plural layers in parallel with a surface having the metal film (or conductive film) of the semiconductor wafer (substrate). The detection coil may be curved so as to have a predetermined thickness greater than the diameter of the wire or the conductive material in a row direction by winding the wire or the conductive material in a spiral fashion by plural layers so as to be closer to (or away from) the substrate gradually.

In a preferred aspect of the present invention, at least one of the plurality of exciting coils comprises a coil formed by winding a wire or a conductive material by a single row and plural layers, the row being defined as a direction perpendicular to the substrate and the layer being defined as a direction parallel to the substrate.

According to the eddy current sensor of the present invention, since at least one of the plurality of exciting coils of the eddy current sensor comprises a coil formed by winding a wire or a conductive material in a single row and plural layers, even if the inductance of the coil becomes larger, the capacitance does not become large. Therefore, high resonance frequency can be obtained, and a thin film can be detected stably even if the oscillation frequency is increased.

Further, according to the eddy current sensor of the present invention, since at least one of the plurality of exciting coils of the eddy current sensor comprises a coil formed by winding a wire or a conductive material in a single row and plural layers, the exciting coil can be brought close to the substrate, and the eddy current can be flowed through the substrate, thus improving sensor sensitivity.

In a preferred aspect of the present invention, at least one of the plurality of dummy coils comprises a coil formed by winding a wire or a conductive material by a single row and plural layers, the row being defined as a direction perpendicular to the substrate and the layer being defined as a direction parallel to the substrate.

In a preferred aspect of the present invention, at least one of the detection coil, the exciting coil and the dummy coil comprises plural coils formed by winding a wire or a conductive material by a single row and plural layers and connected in series.

According to the present invention, plural coils having a single row and plural layers are connected in series, and thus synthetic inductance of coils is equal to the sum of the inductance of plural coils and mutual inductance between the adjacent coils. Therefore, synthetic inductance of coils increases, and sensor outputs of the entire coils increase, and thus a metal film can be detected with high accuracy.

In a preferred aspect of the present invention, the exciting coil is curved so as to be closer to the substrate toward a radially outward edge of the exciting coil.

According to the present invention, the exciting coil comprises a coil formed by winding a wire or a conductive material such that the coil is curved in the form of concave sphere so as to be dented toward the dummy coil side at a radially inner side and to be closer to the detection coil side toward a radially outer side. In this manner, since the exciting coil is curved in the form of concave sphere, an oscillation magnetic field can converge on the central area and the sensor sensitivity can be improved.

In a preferred aspect of the present invention, the detection coil, the exciting coil and the dummy coil are housed in a tubular member made of a material having a high-magnetic permeability.

According to the present invention, a magnetic flux from the exciting coil forms a path (magnetic circuit) so as to pass through the tubular member having a high-magnetic permeability, which is located around the exciting coil and then pass through the metal film (or conductive film) to be measured. Since the magnetic flux does not pass through a member in an installation environment, the magnetic flux is not attenuated. Thus, an eddy current can effectively be generated in the metal film (or conductive film), and the metal film (or conductive film) can be measured with high sensitivity.

According to a third aspect of the present invention, there is provided a polishing method of polishing a metal film or a conductive film on a substrate as an object to be polished by pressing the substrate against a polishing surface on a rotating polishing table, the polishing method comprising: scanning a surface, being polished, of the substrate by an eddy current sensor provided in the polishing table while the polishing table is rotated, while polishing of the substrate; and monitoring an output of the eddy current sensor obtained by scanning the surface, being polished, of the substrate to monitor a film thickness of the metal film or the conductive film from the output of the eddy current sensor; wherein the eddy current sensor comprises a plurality of coils having different sizes formed by winding a wire or a conductive material, and the plurality of coils are configured to detect respective eddy currents generated in two or more areas which comprise a first area on the surface, being polished, of the substrate, and a second area including the first area and having a larger area than the first area.

According to the third aspect of the present invention, while the eddy current sensor passes through under the semiconductor wafer by rotation of the polishing table, the eddy current sensor outputs a certain voltage value or the like in response to the metal film (or conductive film) of the substrate. By monitoring the outputs of the eddy current sensor, the film thickness of the metal film or the conductive film can be monitored. During this time, the plural coils sweep across the surface, being polished, of the substrate on the same locus, thus can measure the metal film or the conductive film on the same locus simultaneously and continuously. Specifically, on the same locus, one of the coils can measure the metal film or the conductive film by detecting the eddy current in a small area (first area) on the target metal film or the conductive film, and the other coils can measure the metal film or the conductive film by detecting the eddy current in a large area (second area) including the small area (first area).

According to a fourth aspect of the present invention, there is provided a polishing method of polishing a metal film or a conductive film on a substrate as an object to be polished by pressing the substrate against a polishing surface on a rotating polishing table, the polishing method comprising: scanning a surface, being polished, of the substrate by an eddy current sensor provided in the polishing table while the polishing table is rotated, while polishing of the substrate; and monitoring an output of the eddy current sensor obtained by scanning the surface, being polished, of the substrate to monitor a film thickness of the metal film or the conductive film from the output of the eddy current sensor; wherein the eddy current sensor comprises a plurality of coils having different sizes formed by winding a wire or a conductive material, and the plurality of coils are configured to detect respective eddy currents of respective areas on the surface, being polished, of the substrate.

According to the fourth aspect of the present invention, while the eddy current sensor passes through under the semiconductor wafer by rotation of the polishing table, the eddy current sensor outputs a certain voltage value or the like in response to the metal film (or conductive film) of the substrate. By monitoring the outputs of the eddy current sensor, the film thickness of the metal film or the conductive film can be monitored. During this time, the plural coils sweep across the surface, being polished, of the substrate on the same locus, thus can measure the metal film or the conductive film on the same locus simultaneously and continuously. During this time, the plurality of coils can detect the eddy currents at respective areas of the surface, being polished, of the substrate. Therefore, the metal film or the conductive film can be measured at the respective areas (for example, an edge area, the central area) of the surface, being polished, of the substrate, and the area which can be detected in the edge area of the substrate is widened. Further, the measured results can be fed back and polishing pressures can be controlled at the respective areas of the surface, being polished, of the substrate, thereby achieving a desired polishing profile.

In a preferred aspect of the present invention, the plurality of coils comprise a plurality of detection coils configured to detect the respective eddy currents generated in the metal film or the conductive film.

In a preferred aspect of the present invention, the plurality of coils comprise a sensor having a large outer sensor diameter and a sensor having a small outer sensor diameter, the polishing method comprising: monitoring an output of the sensor having a large outer sensor diameter; detecting a polishing end point from a change in the output of the sensor having a large outer sensor diameter; and monitoring an output of the sensor having a small outer sensor diameter after detecting the polishing end point and performing monitoring of the remaining film for detecting a film left on a part of the substrate.

According to the polishing method of the present invention, the sensor comprising the detection coil having a large outer diameter serves as a sensor having a low sensitivity, and it can detect the remaining film accurately over the entire surface, being polished, of the substrate and detect the polishing end point stably. The sensor comprising the detection coil having a small outer diameter serves as a sensor having a high sensitivity, and it can detect the remaining film even when the target metal film or the conductive film becomes thin or the remaining area of the metal film or the conductive film becomes small. Therefore, the sensor comprising the detection coil having a small outer diameter can detect detailed distribution state of the remaining film on the surface, being polished, of the substrate, and can also detect the thin film at the edge area of the substrate.

In a preferred aspect of the present invention, the plurality of coils comprise a coil having a small median coil diameter and a coil having a large median coil diameter, the median coil diameter being defined as an arithmetic average of an inner diameter and an outer diameter of the coil; a sensor comprising the coil having a small median coil diameter constitutes a sensor having a small sensor diameter; and a sensor comprising the coil having a large median coil diameter constitutes a sensor having a large sensor diameter; the polishing method comprising: monitoring an output of the sensor having a large sensor diameter; detecting a polishing end point from a change in the output of the sensor having a large sensor diameter; monitoring an output of the sensor having a small sensor diameter after detecting the polishing end point and performing monitoring of the remaining film for detecting a film left on a part of the substrate.

According to the polishing method of the present invention, the sensor comprising the detection coil having a large median diameter serves as a sensor having a low sensitivity, and it can detect the remaining film accurately over the entire surface, being polished, of the substrate and detect the polishing end point stably. The sensor comprising the detection coil having a small median diameter serves as a sensor having a high sensitivity, and it can detect the remaining film even when the target metal film or the conductive film becomes thin or the remaining area of the metal film or the conductive film becomes small. Therefore, the sensor comprising the detection coil having a small median diameter can detect detailed distribution state of the remaining film on the surface, being polished, of the substrate, and can also detect the thin film at the edge area of the substrate.

According to a fifth aspect of the present invention, there is provided an eddy current sensor for detecting an eddy current generated in a metal film or a conductive film, the eddy current sensor comprising: an inner coil; and an outer coil spaced outwardly from the inner coil so as to surround the inner coil; wherein the inner coil and the outer coil are configured to detect respective eddy currents generated in the metal film or the conductive film.

According to the present invention, the following effects can be achieved.

1) Since the plurality of coils for detecting the eddy current in the eddy current sensor comprise a coil having a small outer diameter (or median coil diameter) and a coil having a large outer diameter (or median coil diameter), the plurality of coils can detect respective eddy currents generated in two or more areas which comprise a small area (first area) and a large area (second area) including the small area (first area) on the substrate. Therefore, the eddy currents detected respectively and simultaneously at two or more areas which have an overlapping area can be compared, and the metal film or the conductive film can be detected with high accuracy.

2) The sensor comprising the detection coil having a small outer diameter (or median coil diameter) serves as a sensor having a high sensitivity, and it can detect the target remaining film even when the metal film or the conductive film becomes thin or the remaining area of the metal film or the conductive film becomes small. Therefore, the detection coil having a small outer diameter (or median coil diameter) can detect detailed distribution state of the remaining film on the surface, being polished, of the substrate, and can also detect the thin film at the edge area of the substrate. The sensor comprising the detection coil having a large outer diameter (or median coil diameter) serves as a sensor having a low sensitivity, and it can detect the remaining film over the entire surface, being polished, of the substrate and can detect the polishing end point stably.

3) The plurality of coils can detect the eddy currents at respective areas of the surface, being polished, of the substrate. Therefore, the metal film or the conductive film can be measured at the respective areas (for example, an edge area, the central area) of the surface, being polished, of the substrate, and the area which can be detected in the edge area of the substrate is widened. Further, the measured results can be fed back and polishing pressures can be controlled at the respective areas of the surface, being polished, of the substrate, thereby achieving a desired polishing profile.

4) Since the detection coil of the eddy current sensor comprises a coil formed by winding a wire or a conductive material in a single row and plural layers, the detection coil can be brought close to the substrate, and capacitance component between lines can be small, thus improving sensor sensitivity. Therefore, the thin metal film (or thin conductive film) on the substrate such as a semiconductor wafer can be detected without increasing oscillation frequency, amplification degree of an internal circuit and exciting voltage of the eddy current sensor.

5) In the case where the remaining film is detected by performing an inspection on whether or not there is a remaining film such as a metal film (or conductive film) on a substrate during polishing, additional polishing is performed as it is, and thus processing time can be shortened. Further, in the case where the remaining film is detected, because the controller for controlling the entire CMP process controls additional polishing time or the remaining film condition, it is possible to change the polishing condition of the subsequent object to be polished to the optimum condition.

BRIEF DESCRIPTION OF THE DRAWINGS

FIG. 10A is a schematic views showing an example in which inductance of a coil (L of a coil) wound by a single row and N-layers is changed;

FIG. 10B is a schematic views showing an example in which inductance of a coil (L of a coil) wound by a single row and N-layers is changed;

FIG. 20A is a schematic view showing a circuit configuration of coils of a sensor coil;

FIG. 20B is a schematic view showing a circuit configuration of coils of a sensor coil;

FIG. 20C is a schematic view showing a circuit configuration of coils of a sensor coil;

FIG. 23A is a graph showing the relationship between a locus described when the eddy current sensor scans a surface (surface to be polished) of the semiconductor wafer W and outputs of the eddy current sensor;

FIG. 23B is a graph showing outputs of the eddy current sensor when the polishing of the semiconductor wafer is started;

FIG. 23C is a graph showing outputs of the eddy current sensor after an elapse of a predetermined time from the start of polishing the semiconductor wafer;

FIG. 24 is a view showing the relationship between a polishing process from starting polishing of the semiconductor wafer to clearing (removing) of a metal film (or conductive film) on the central part of the semiconductor wafer and outputs of the eddy current sensor;

FIG. 31 is a view showing an embodiment in which a sampling interval can be changed in accordance with sizes of the pressure chambers.

DETAILED DESCRIPTION OF THE PREFERRED EMBODIMENTS

Figure 1:
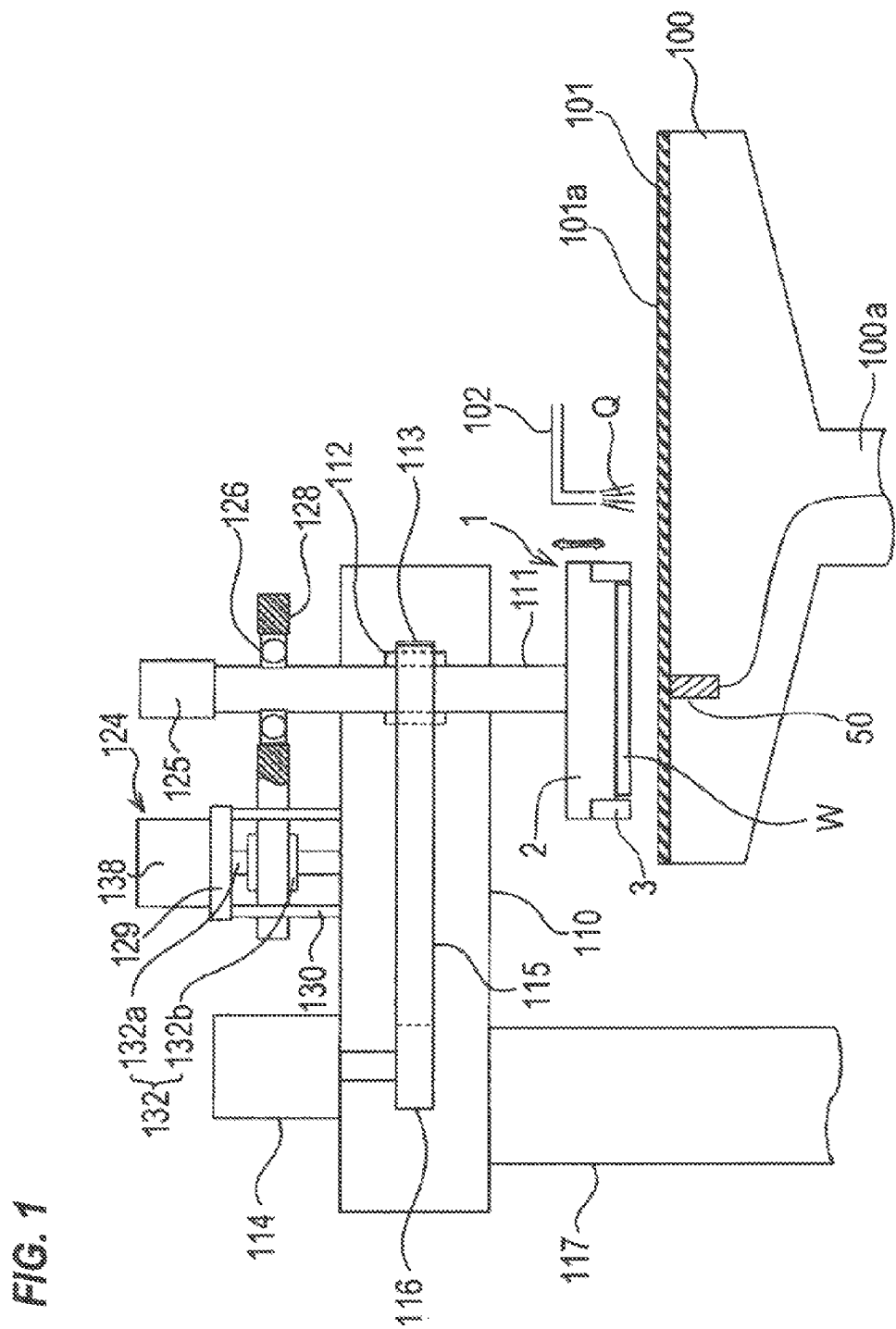
FIG. 1 is a schematic view showing an entire structure of a polishing apparatus according to the present invention.

A polishing apparatus according to embodiments of the present invention will be described below with reference to FIGS. 1 through 31. Like or corresponding structural elements are denoted by like or corresponding reference numerals in FIGS. 1 through 31 and will not be described below repetitively.

FIG. 1 is a schematic view showing an entire structure of a polishing apparatus according to the present invention. As shown in FIG. 1, the polishing apparatus comprises a polishing table 100, and a top ring 1 for holding a substrate such as a semiconductor wafer as an object to be polished and pressing the substrate against a polishing surface on the polishing table.

The polishing table 100 is coupled via a table shaft 100a to a motor (not shown) disposed below the polishing table 100. Thus, the polishing table 100 is rotatable about the table shaft 100a. A polishing pad 101 is attached to an upper surface of the polishing table 100. An upper surface 101a of the polishing pad 101 constitutes a polishing surface configured to polish a semiconductor wafer W. A polishing liquid supply nozzle 102 is provided above the polishing table 100 to supply a polishing liquid Q onto the polishing pad 101 on the polishing table 100. As shown in FIG. 1, an eddy current sensor 50 is embedded in the polishing table 100.

The top ring 1 basically comprises a top ring body 2 for pressing a semiconductor wafer W against the polishing surface 101a, and a retainer ring 3 for holding an outer peripheral edge of the semiconductor wafer W to prevent the semiconductor wafer W from being slipped out of the top ring.

The top ring 1 is connected to a top ring shaft 111, and the top ring shaft 111 is vertically movable with respect to a top ring head 110 by a vertically movable mechanism 124. When the top ring shaft 111 moves vertically, the top ring 1 is lifted and lowered as a whole for positioning with respect to the top ring head 110. A rotary joint 125 is mounted on the upper end of the top ring shaft 111.

The vertical movement mechanism 124, which vertically moves the top ring shaft 111 and the top ring 1, has a bridge 128 supporting the top ring shaft 111 in a manner such that the top ring shaft 111 is rotatable via a bearing 126, a ball screw 132 mounted on the bridge 128, a support stage 129 which is supported by poles 130, and an AC servomotor 138 provided on the support stage 129. The support stage 129, which supports the servomotor 138, is fixed to the top ring head 110 via the poles 130.

The ball screw 132 has a screw shaft 132a which is coupled to the servomotor 138, and a nut 132b into which the screw shaft 132a is threaded. The top ring shaft 111 is configured to be vertically movable together with the bridge 128. Accordingly, when the servomotor 138 is driven, the bridge 128 is vertically moved through the ball screw 132. As a result, the top ring shaft 111 and the top ring 1 are vertically moved.

Further, the top ring shift 111 is connected to a rotary sleeve 112 by a key (not shown). The rotary sleeve 112 has a timing pulley 113 fixedly disposed therearound. A top ring motor 114 is fixed to the top ring head 110. The timing pulley 113 is operatively coupled to a timing pulley 116 provided on the top ring motor 114 by a timing belt 115. Therefore, when the top ring motor 114 is driven, the timing pulley 116, the timing belt 115 and the timing pulley 113 are rotated to rotate the rotary sleeve 112 and the top ring shaft 111 in unison with each other, thus rotating the top ring 1. The top ring head 110 is supported on a top ring head shaft 117 which is rotatably supported by a flame (not shown).

In the polishing apparatus constructed as shown in FIG. 1, the top ring 1 is configured to hold a substrate such as a semiconductor wafer W on its lower surface. The top ring head 110 is pivotable about the top ring shaft 117. Thus, the top ring 1, which holds the semiconductor wafer W on its lower surface, is moved from a position at which the top ring 1 receives the semiconductor wafer W to a position above the polishing table 100 by pivotable movement of the top ring head 110. Then, the top ring 1 is lowered to press the semiconductor wafer W against a surface (polishing surface)

101a of the polishing pad 101. At this time, while the top ring 1 and the polishing table 100 are respectively rotated, a polishing liquid is supplied onto the polishing pad 101 from the polishing liquid supply nozzle 102 provided above the polishing table 100. In this manner, the semiconductor wafer W is brought into sliding contact with the polishing surface 101a of the polishing pad 101. Thus, a surface of the semiconductor wafer W is polished.

Figure 2:
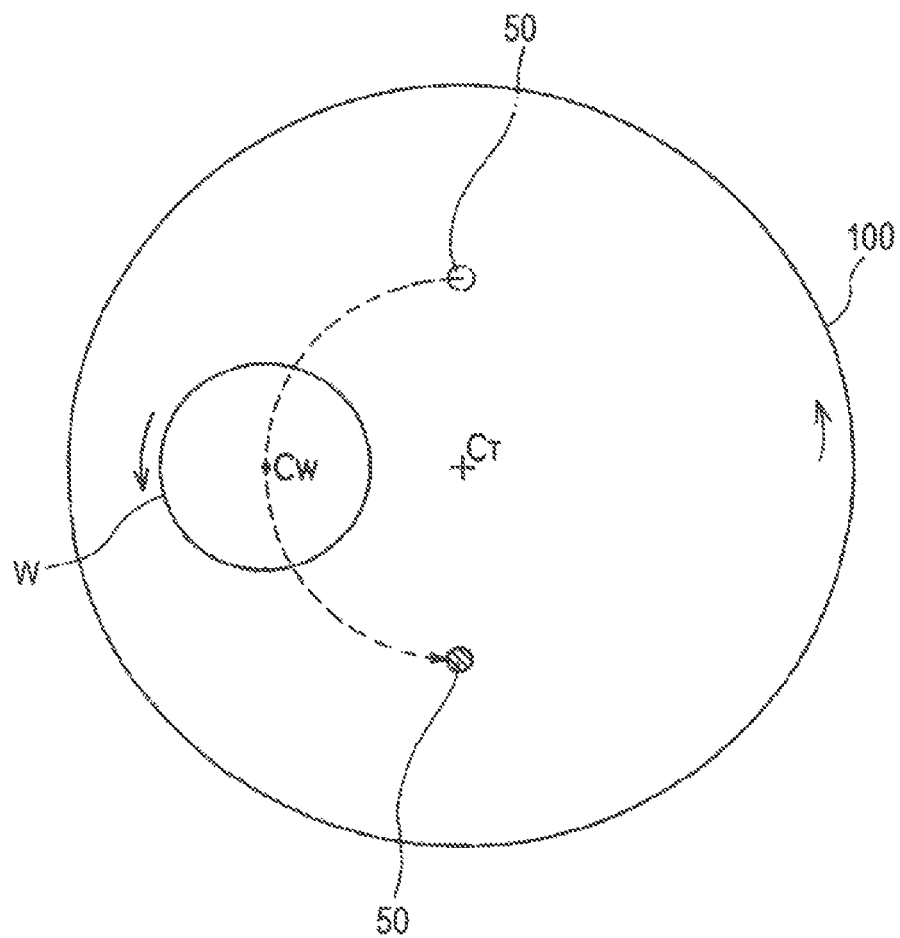
FIG. 2 is a plan view showing the relationship between a polishing table, an eddy current sensor and a semiconductor wafer.

FIG. 2 is a plan view showing the relationship between the polishing table 100, the eddy current sensor 50 and the semiconductor wafer W. As shown in FIG. 2, the eddy current sensor 50 is positioned so as to pass through the center Cw of the semiconductor wafer W held by the top ring 1 during polishing. The symbol $C_T$ represents a rotation center of the polishing table 100. For example, while the eddy current sensor 50 passes through under the semiconductor wafer W, the eddy current sensor 50 is capable of detecting a metal film (conductive film) such as a copper layer on the semiconductor wafer W continuously on a passage locus (scanning line).

Next, the eddy current sensor 50 provided on the polishing apparatus according to the present invention will be described in detail with reference to FIGS. 3 through 19.

Figure 3A:
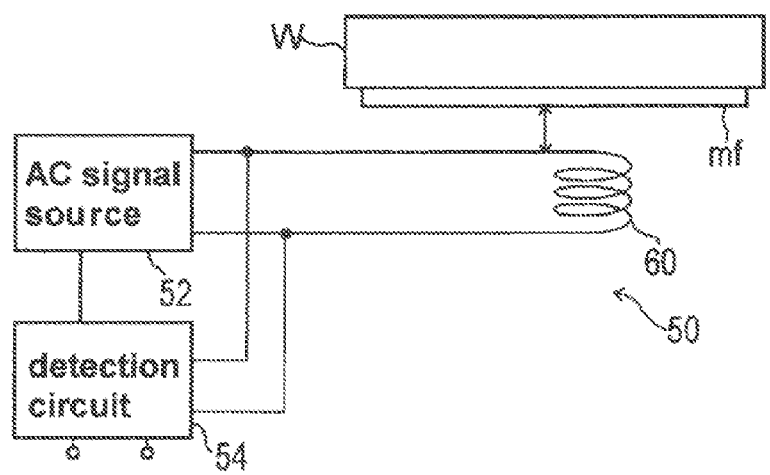
FIG. 3A is a block diagram showing the basic structure of the eddy current sensor.
Figure 3B:
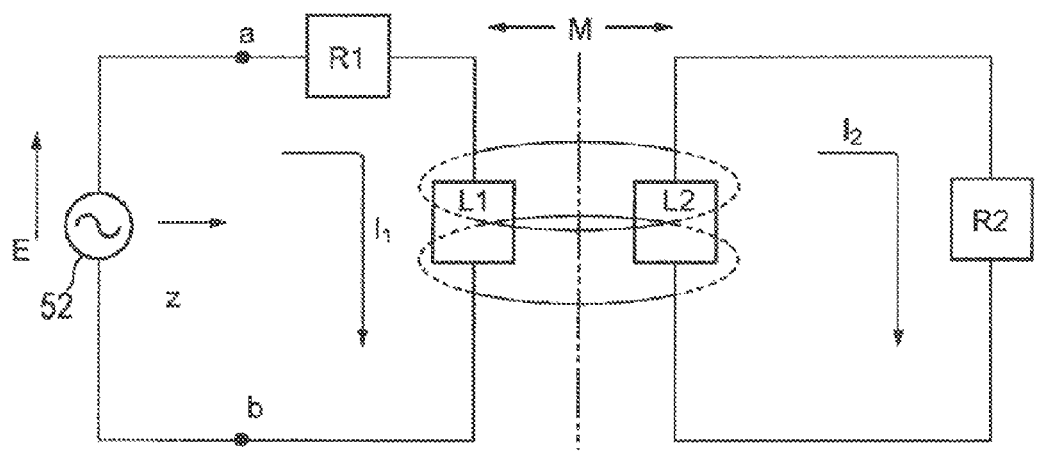
FIG. 3B is an equivalent circuit diagram of the eddy current sensor.

FIGS. 3A and 3B are views showing a structure of the eddy current sensor 50, FIG. 3A is a block diagram showing the structure of the eddy current sensor 50, and FIG. 3B is an equivalent circuit diagram of the eddy current sensor 50.

As shown in FIG. 3A, the eddy current sensor 50 comprises a sensor coil 60 disposed near a metal film (or conductive film) mf as an object to be detected, and an AC signal source 52 connected to the sensor coil 60. The metal film (or conductive film) mf as an object to be detected is, for example, a thin film of Cu, Al, Au, W, or the like formed on the semiconductor wafer W. The sensor coil 60 is a detection coil disposed near the metal film (or conductive film) to be detected, and is spaced from the metal film (or conductive film) by a distance of about 1.0 to 4.0 mm, for example.

Examples of the eddy current sensor include a frequency-type eddy current sensor which detects a metal film (or conductive film) mf based on a change in oscillation frequency that is caused by an eddy current induced in the metal film (or conductive film) mf, and an impedance-type eddy current sensor which detects a metal film (or conductive film) based on a change in impedance. Specifically, in the frequency-type eddy current sensor, as shown in the equivalent circuit of FIG. 3B, when an eddy current $I_2$ is changed, an impedance Z is changed, thus causing a change in the oscillation frequency of the signal source (variable-frequency oscillator) 52. A detection circuit 54 detects the change in the oscillation frequency, thereby detecting a change of the metal film (or conductive film). In the impedance-type eddy current sensor, as shown in the equivalent circuit of FIG. 3B, when the eddy current $I_2$ is changed, the impedance Z is changed. When the impedance Z as viewed from the signal source (variable-frequency oscillator) 52 is changed, the detection circuit 54 detects the change in the impedance Z, thereby detecting a change of the metal film (or conductive film).

In the impedance-type eddy current sensor, signal outputs X and Y, a phase, and a combined impedance Z are derived as describe later. From the frequency F, the impedances X and Y, or the like, it is possible to obtain the measurement information of a metal film (or conductive film) Cu, Al, Au or W. The eddy current sensor 50 is embedded in the polishing table 100 near its surface and faces the semiconductor wafer to be polished through the polishing pad, thereby detecting a change of the metal film (or conductive film) on the semiconductor wafer based on an eddy current flowing through the metal film (or conductive film).

The frequency of the eddy current sensor may be obtained from a single radio wave, a mixed radio wave, an AM radio wave, an FM radio wave, a sweep output of a function generator, or a plurality of oscillation frequency sources. It is preferable to select a highly sensitive oscillation frequency and modulation method according to the type of metal film to be measured.

The impedance-type eddy current sensor will be described concretely below. The AC signal source 52 comprises an oscillator for generating a fixed frequency in the range of about 2 to 8 MHZz. A crystal quartz oscillator may be used as such an oscillator. When an alternating voltage is supplied from the AC signal source 52 to the sensor coil 60, current $I_1$ flows through the sensor coil 60. When the current flows through the sensor coil 60 disposed near the metal film (or conductive film) mf, a magnetic flux interlinks with the metal film (or conductive film) mf, thus forming a mutual inductance M therebetween to induce an eddy current $I_2$ in the metal film (or conductive film) mf. Here, R1 represents an equivalent resistance at a primary side including the sensor coil, and L1 represents a self-inductance at a primary side also including a sensor coil. In the metal film (or conductive film) mf, R2 represents an equivalent resistance corresponding to the eddy current loss, and L2 represents a self-inductance. The impedance Z as viewed from terminals "a" and "b" of the AC signal source 52 toward the sensor coil is changed depending on the magnitude of the eddy current loss caused in the metal film (or conductive film) mf.

Figure 4A:
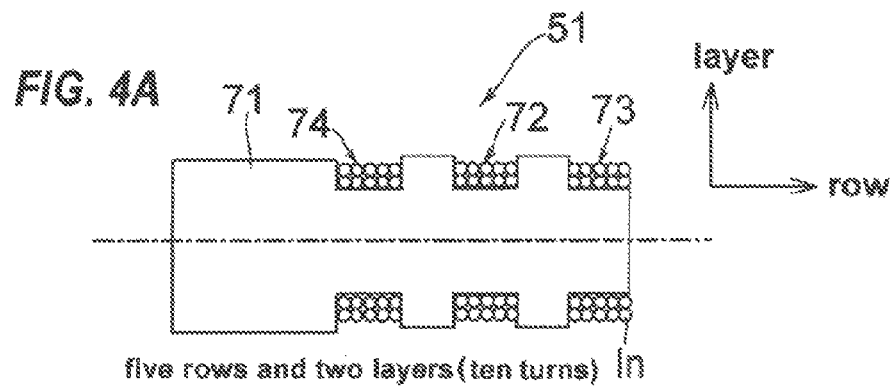
FIGS. 4A, 4B and 4C are views showing comparison between a sensor coil of a conventional eddy current sensor and sensor coils of an eddy current sensor of the present invention, FIG. 4A being a schematic view showing a structural example of the sensor coil used in the conventional eddy current sensor, FIG. 4B being a schematic view showing a structural example of the sensor coils of the eddy current sensor of the present invention, and FIG. 4C being a schematic plan view showing detection coils of the eddy current sensor of the present invention.
Figure 4B:
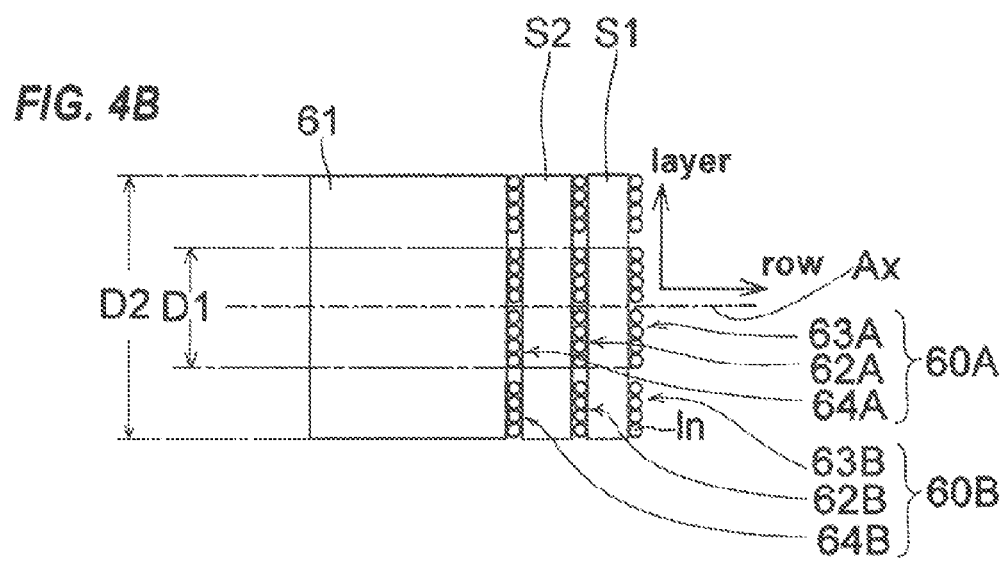
Figure 4C:
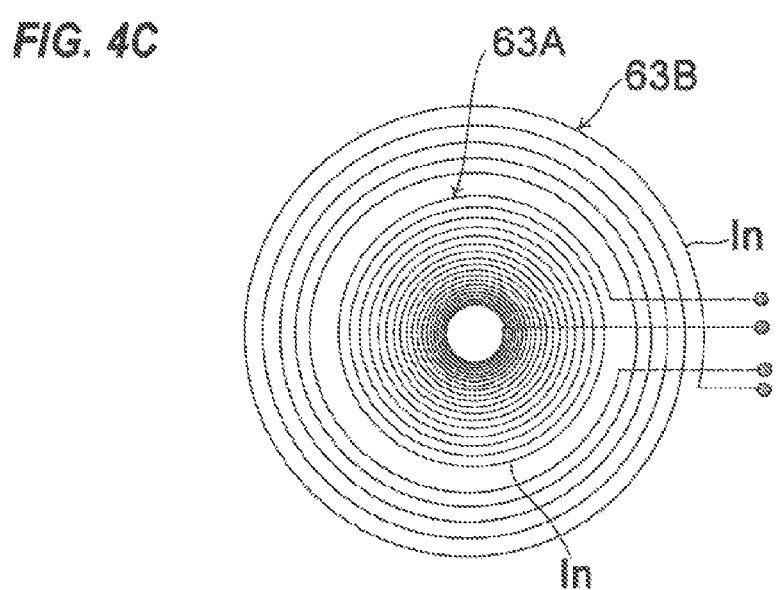

FIGS. 4A, 4B and 4C are views showing comparison between a sensor coil of a conventional eddy current sensor and sensor coils of an eddy current sensor of the present invention. FIG. 4A is a schematic view showing a structural example of the sensor coil used in the conventional eddy current sensor, FIG. 4B is a schematic view showing a structural example of the sensor coils of an eddy current sensor 50 of the present invention, and FIG. 4C is a schematic plan view showing detection coils of the eddy current sensor 50 of the present invention.

As shown in FIG. 4A, the sensor coil 51 of the conventional eddy current sensor comprises a coil for generating an eddy current in the metal film (or conductive film), and a coil, separated from the above coil, for detecting the eddy current in the metal film (or conductive film). Specifically, the sensor coil 51 comprises three coils 72, 73 and 74 wound around a bobbin 71. In order to obtain sensor sensibility, it is necessary to increase the number of turns of the coil. Therefore, each of the three coils 72, 73 and 74 in the sensor coil 51 comprises a coil formed by winding a wire ln in a solenoidal fashion by five rows and two layers (10 turns) around an outer circumference of the bobbin 71, the row being defined as a direction perpendicular to the semiconductor wafer (substrate) W and the layer being defined as a direction parallel to the semiconductor wafer (substrate) W. The central coil 72 is an exciting coil (oscillation coil) connected to the AC signal source 52. The AC signal source 52 supplies voltage to the exciting coil 72, and hence the exciting coil 72 produces a magnetic field to generate an eddy current in the metal film (or conductive film) mf on the semiconductor wafer (substrate) W disposed near the exciting coil 72. The detection coil 73 is disposed at the metal film (or conductive film) side of the bobbin 71 and detects a magnetic field produced by the eddy current generated in the metal film (or conductive film). The dummy coil (balancing coil) 74 is disposed at the opposite side of the detection coil 73 with respect to the exciting coil 72.

On the other hand, as shown in FIG. 4B, the eddy current sensor 50 of the present invention comprises two sensor coils 60A and 60B. The two sensor coils 60A and 60B are provided separately from each other such that the outer sensor coil 60B surrounds the inner sensor coil 60A. The inner sensor coil 60A comprises three coils 62A, 63A and 64A which are not wound around a bobbin 61. Each of the three coils 62A, 63A and 64A in the sensor coil 60A comprises a coil formed by winding a wire or a conductive material ln in a spiral fashion by a single row and N-layers, the row being defined as a direction perpendicular to the semiconductor wafer (substrate) W and the layer being defined as a direction parallel to the semiconductor wafer (substrate) W. More specifically, when the row is defined as a direction perpendicular to a surface having a metal film (or conductive film) of the semiconductor wafer (substrate) W and the layer is defined as a direction parallel to the surface having the metal film (or conductive film) of the semiconductor wafer (substrate) W, each of the three coils 62A, 63A and 64A comprises a coil formed by winding a wire or a conductive material ln in a spiral fashion by a single row and N-layers. N is an integer not less than 2, and for example, if the number of the turns is more than or equal to the conventional one, N is not less than 11.

The central coil 62A of the three coils 62A, 63A and 64A is an exciting coil (oscillation coil) connected to the AC signal source 52. The AC signal source 52 supplies voltage to the exciting coil 62A, and hence the exciting coil 62A produces a magnetic field to generate an eddy current in the metal film (or conductive film) mf on the semiconductor wafer W disposed near the exciting coil 62A. The detection coil 63A is disposed at the metal film (or conductive film) side and detects a magnetic field produced by the eddy current generated in the metal film (or conductive film). The dummy coil (balancing coil) 64A is disposed at the opposite side of the detection coil 63A with respect to the exciting coil 62A. A spacer S1 is interposed between the exciting coil 62A and the detection coil 63A to keep a distance between the exciting coil 62A and the detection coil 63A constant. A spacer S2 is interposed between the exciting coil 62A and the dummy coil 64A to keep a distance between the exciting coil 62A and the dummy coil 64A constant. A bobbin 61 is disposed adjacent to the dummy coil 64A. As long as a distance is provided between the exciting coil 62A and the detection coil 63A and between the exciting coil 62A and the dummy coil 64A, only space is sufficient without providing a spacer.

The outer sensor coil 60B comprises three coils 62B, 63B and 64B which are not wound around the bobbin 61. Each of the three coils 62B, 63B and 64B in the sensor coil 60B comprises a coil formed by winding a wire or conductive material ln in a spiral fashion by a single row and N-layers, the row being defined as a direction perpendicular to the semiconductor wafer (substrate) W and the layer being defined as a direction parallel to the semiconductor wafer (substrate) W. More specifically, when the row is defined as a direction perpendicular to a surface having a metal film (or conductive film) of the semiconductor wafer (substrate) W and the layer is defined as a direction parallel to the surface having the metal film (or conductive film) of the semiconductor wafer (substrate) W, each of the three coils 62B, 63B and 64B comprises a coil formed by winding a wire or conductive material ln in a spiral fashion by a single row and N-layers. N is an integer not less than 2, and for example, if the number of the turns is more than or equal to the conventional one, N is not less than 11.

The central coil 62B of the three coils 62B, 63B and 64B is an exciting coil (oscillation coil) connected to the AC signal source (not shown) which is provided separately and has the same configuration as the AC signal source 52 shown in FIG. 3A. The AC signal source supplies voltage to the exciting coil 62B, and hence the exciting coil 62B produces a magnetic field to generate an eddy current in the metal film (or conductive film) mf on the semiconductor wafer W disposed near the exciting coil 62B. The detection coil 63B is disposed at the metal film (or conductive film) side and detects a magnetic field produced by the eddy current generated in the metal film (or conductive film). The dummy coil (balancing coil) 64B is disposed at the opposite side of the detection coil 63B with respect to the exciting coil 62B. A spacer S1 is interposed between the exciting coil 62B and the detection coil 63B to keep a distance between the exciting coil 62B and the detection coil 63B constant. A spacer S2 is interposed between the exciting coil 62B and the dummy coil 64B to keep a distance between the exciting coil 62B and the dummy coil 64B constant. A bobbin 61 is disposed adjacent to the dummy coil 64B. As long as a distance is provided between the exciting coil 62B and the detection coil 63B and between the exciting coil 62B and the dummy coil 64B, only space is sufficient without providing a spacer.

FIG. 4C is a schematic plan view showing detection coils 63A and 63B of the two sensor coils 60A, 60B. As shown in FIG. 4C, the two detection coils 63A and 63B are provided separately from each other such that the outer detection coil 63B surrounds the inner detection coil 63A. Each of the two detection coils 63A and 63B comprises a coil formed by winding a wire or conductive material around a common axis Ax (see FIG. 4B) as a central axis which is perpendicular to a surface having a metal film (or conductive film) of the semiconductor wafer (substrate) W. The two detection coils 63A and 63B are provided separately from each other in a radial direction which is perpendicular to the axis Ax. As described above, the inner detection coil 63A comprises the coil formed by winding the wire or conductive material ln radially in a spiral fashion by a single row and N-layers. The detection coil 63A may be flat so as to have a thickness corresponding to only a diameter of the wire or conductive material ln in a row direction (direction perpendicular to a surface of paper in FIG. 4C) by winding the wire or conductive material ln in a spiral fashion by N-layers in parallel with a surface having the metal film (or conductive film) mf of the semiconductor wafer (substrate) W. The detection coil 63A may be curved so as to have a predetermined thickness greater than the diameter of the wire or conductive material ln in a row direction by winding the wire or conductive material ln in a spiral fashion by N-layers so as to be closer to (or away from) the semiconductor wafer (substrate) W gradually.

The outer detection coil 63B also comprises the coil formed by winding the wire or conductive material ln radially in a spiral fashion by a single row and N-layers. The detection coil 63B may be flat so as to have a thickness corresponding to only a diameter of the wire or conductive material ln in a row direction (direction perpendicular to a surface of paper in FIG. 4C) by winding the wire or conductive material ln in a spiral fashion by N-layers in parallel with a surface having the metal film (or conductive film) mf of the semiconductor wafer (substrate) W. The detection coil 63B may be curved so as to have a predetermined thickness greater than the diameter of the wire or conductive material ln in a row direction by winding the wire or conductive material ln in a spiral fashion by N-layers so as to be closer to (or away from) the semiconductor wafer (substrate) W gradually.

Although the two detection coils 63A and 63B are shown in FIG. 4C, the two exciting coils 62A, 62B also have the same configuration as in FIG. 4C. Each of the two exciting coils 62A and 62B comprises a coil formed by winding a wire or conductive material around the common axis Ax (see FIG. 4B) as a central axis. The two exciting coils 62A and 62B are provided separately from each other in a radial direction which is perpendicular to the axis Ax. The two dummy coils 64A, 64B also have the same configuration as in FIG. 4C. Each of the two dummy coils 64A and 64B comprises a coil formed by winding a wire or conductive material around the common axis Ax (see FIG. 4B) as a central axis. The two dummy coils 64A and 64B are provided separately from each other in a radial direction which is perpendicular to the axis Ax.

Further, each of the coils 62A, 63A, 64A in the sensor coil 60A and each of the coils 62B, 63B, 64B in the sensor coil 60B may be configured to connect m number of coils, in series, formed by winding the wire or conductive material ln in a spiral fashion by a single row and N-layers shown in FIG. 4C. In this case, m is an integer not less than 2. In the case where m number of coils having a single row and N-layers are connected in series, if the respective coils contact each other, then capacitance component increases. Therefore, it is preferable that m number of coils having a single row and N-layers are arranged in a row direction (direction perpendicular to the substrate) and a clearance (gap) is provided between the adjacent coils. A material having a low-dielectric constant or a space may be provided in the clearance.

Figure 5A:
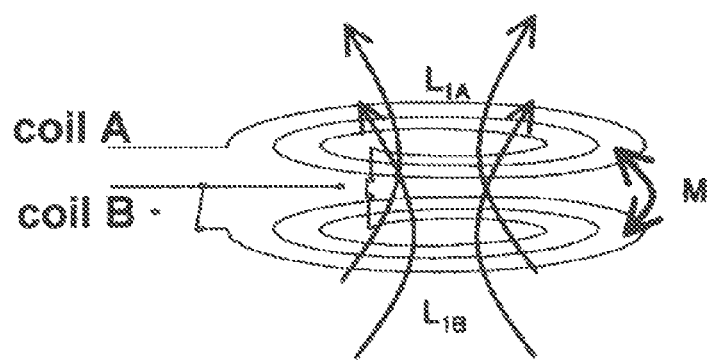
FIG. 5A is a schematic view showing an embodiment in which m-number of coils having a single row and N-layers are connected in series.
Figure 5B:
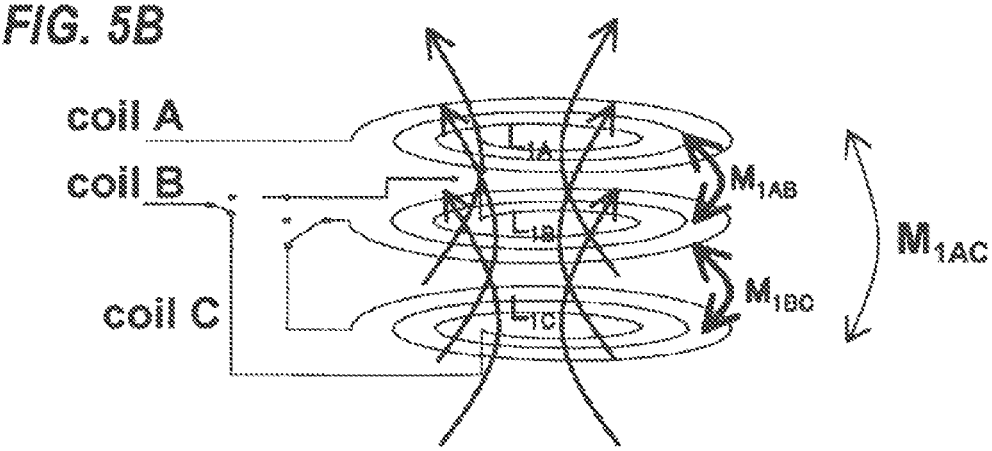
FIG. 5B is a schematic view showing an embodiment in which m-number of coils having a single row and N-layers are connected in series.

FIGS. 5A and 5B are schematic views showing embodiments in which m number of coils having a single row and N-layers are connected in series.

In the embodiment shown in FIG. 5A, a coil A having a single row and N-layers and a coil B having a single row and N-layers are connected in series. In the embodiment of FIG. 5A, inductance $L_{1A}+L_{1B}$ of two rows of coils and mutual inductance M between adjacent coils are obtained. The mutual inductance M between the adjacent coils is expressed by the following equation:

Error! Objects cannot be created from editing field codes.

Here, k is coefficient of coupling, and $L_{1A}$ and $L_{1B}$ are self-inductance [H].

Therefore, in the embodiment shown in FIG. 5A, synthetic inductance becomes $L_0=L_{1A}+L_{1B}+2M$.

In the embodiment shown in FIG. 5B, a coil A having a single row and N-layers, a coil B having a single row and N-layers and a coil C having a single row and N-layers are connected in series. In the embodiment of FIG. 5B, inductance $L_{1A}+L_{1B}+L_{1C}$ of three rows of coils and mutual inductance $M_{1AB}$, $M_{1BC}$, $M_{1AC}$ between adjacent coils are obtained. The mutual inductance $M_{1AB}$, $M_{1BC}$ and $M_{1AC}$ are expressed by the following equations:

$M_{1AB}=k_0\sqrt{L_{1A}\cdot L_{1B}}[H]$ $M_{1BC}=k_1\sqrt{L_{1B}\cdot L_{1C}}[H]$ $M_{1AC}=k_2\sqrt{L_{1A}\cdot L_{1C}}[H]$ Here, $k_0$, $k_1$ and $k_2$ are coefficient of coupling, and $L_{1A}$, $L_{1B}$ and $L_{1C}$ are self-inductance [H].

Therefore, in the embodiment shown in FIG. 5B, synthetic inductance becomes $L_0=L_{1A}+L_{1B}+L_{1C}+2M_{1AB}+2M_{1BC}+2M_{1AC}$.

In FIGS. 5A and 5B, two or three coils having a single row and N-layers are connected in series. In the case where m number of coils having a single row and N-layers are connected in series, synthetic inductance $L_0$ of coils is equal to the sum of the inductance of m rows and mutual inductance between m rows. Therefore, as synthetic inductance of coils increases, sensor output of the entire coil increases, and thus a metal film can be detected with high accuracy.

Further, in the embodiment shown in FIGS. 5A and 5B, by providing a switch between coils having a single row and N-layers, the number of coils which are connected in series can be suitably selected. Therefore, the number of coils (the number of rows) in each of the detection coil 63A (or 63B), the exciting coil 62A (or 62B) and the dummy coil 64A (or 64B) is switched depending on metal film to be detected or film thickness to be detected, and optimum detection can be performed. For example, in the case where film thickness of the metal film is small or resistance value of metal is low, the number of coils (the number of rows) can be increased. In FIGS. 5A and 5B, there may be no space (clearance) between the adjacent coils, but preferably there should be a space (clearance) between the adjacent coils of the coil A, the coil B, the coil C, and the like. Then, a material having a low-dielectric constant may be provided in the space (clearance).

Figure 6:
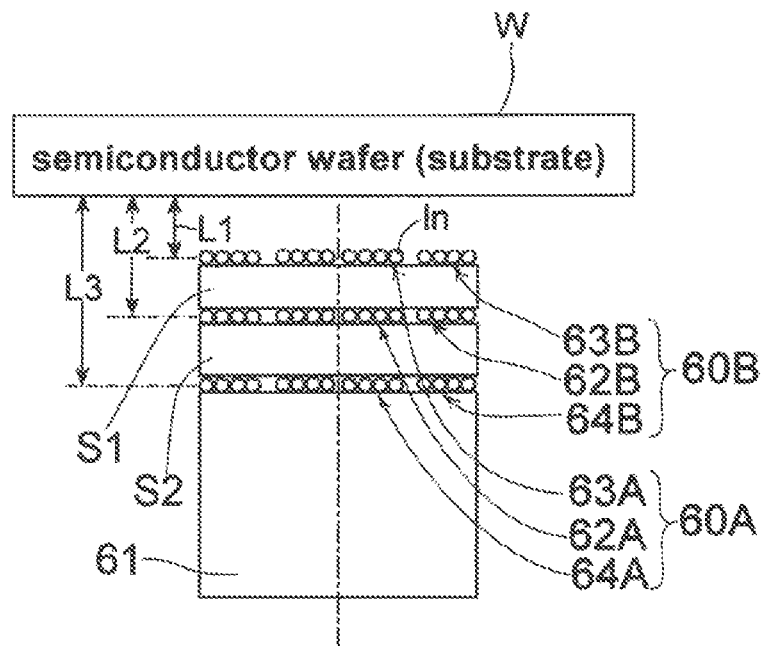
FIG. 6 is a schematic elevational view showing a positional relationship between the sensor coils in the eddy current sensor of the present invention and the semiconductor wafer (substrate)

FIG. 6 is a schematic elevational view showing a positional relationship between the sensor coils 60A, 60B in the eddy current sensor of the present invention and the semiconductor wafer (substrate).

Because the sensor coils 60A, 60B of the present invention do not need to be wound around the bobbin, the number of turns of the coil can be large in a condition that thicknesses of the respective coils 63A, 62A, 64A; 63B, 62B, 64B are thin by winding the respective coils 63A, 62A, 64A; 63B, 62B, 64B in a spiral fashion by a single row and N-layers. Therefore, the distances (L1, L2, L3) between the respective coils 63A, 62A, 64A; 63B, 62B, 64B in the sensor coil 60 and the semiconductor wafer W can be small, and hence the sensor sensitivity is improved. Further, by making the number of turns of the coil large, L component increases and the sensitivity is improved.

In contrast, in the case of the spiral winding of the present invention, because the coil is wound by a single row and N-layers, the capacitance component between lines can be small because of series connection. Because the number of turns of the coil can be large, the resonance frequency is increased while the L component is kept high, and the oscillation frequency can be increased.

Although the spiral winding coil is illustrated in FIGS. 4B and 4C, the same effects can be obtained by other winding as long as the coil is wound by a single row and N-layers.

Figure 7:
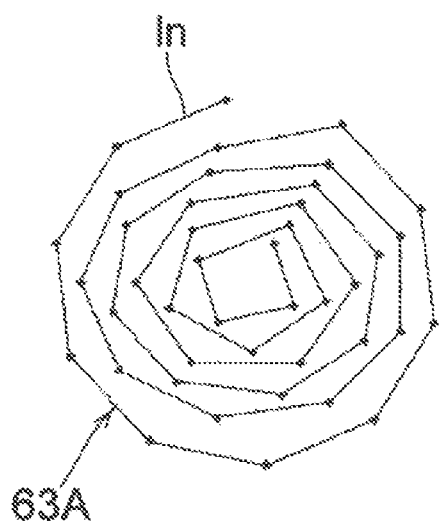
FIG. 7 is a schematic view showing a sensor coil formed by other winding.
Figure 8:
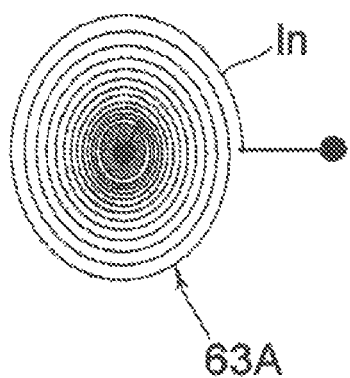
FIG. 8 is a schematic view showing a sensor coil formed by other winding.
Figure 9:
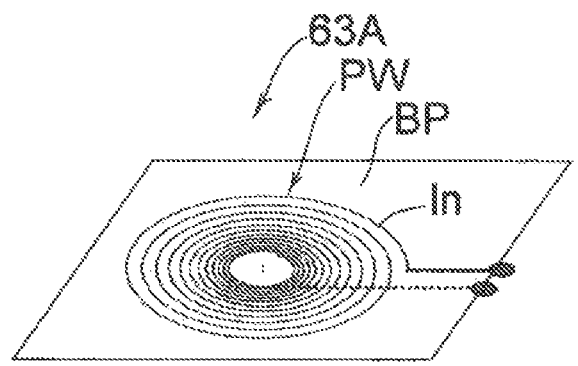
FIG. 9 is a schematic view showing a sensor coil formed by other winding.

FIGS. 7 through 9 are schematic views showing sensor coils having a single row and N-layers formed by other winding.

In the example shown in FIG. 7, the detection coil 63A is formed by winding a wire ln in a polygonal shape by a single row and N-layers. As shown in FIG. 7, as the wire is wound from radially inner side toward radially outer side, the number of the angles of the polygonal shape may increase, or may be the same like a polygonal shape having only triangles or quadrangles.

In the example shown in FIG. 8, the detection coil 63A is formed by winding a wire ln in an elliptical shape by a single row and N-layers.

In the example shown in FIG. 9, the detection coil 63A comprising a pattern coil is formed by printed wiring (PW) applied to a predetermined substrate BP so as to wind a conductive material ln in a spiral fashion by a single row and N-layers. The pattern coil having a single row and N-layers formed by a conductive material ln may be produced by processing such as etching or wire cutting of metal material (Cu film, Cu foil, Cu material or the like), other than the printed wiring. The metal material may be other material such as AL than Cu.

Although several windings of the wire or the conductive material ln are applied to the inner detection coil 63A in the examples shown in FIGS. 7 through 9, such windings can be applied to the outer detection coil 63B and also to the exciting coils 62A, 62B and the dummy coils 64A, 64B.

FIGS. 10A and 10B are schematic views showing examples wherein the inductance of the coil (L of the coil) wound by a single row and N-layers is changed.

In the example shown in FIG. 10A, the detection coil 63A is formed by winding a wire or a conductive material ln in a spiral fashion by a single row and N-layers. As shown in FIG. 10A, the coil wound in a spiral fashion has an outer circumferential end and an inner circumferential end which are connected respectively to terminals T1, T2, and intermediate points which are connected respectively to terminals T3, T4. A coil portion between the terminals T1 and T2 constitutes a coil 1 having the largest coil length. A coil portion between the terminals T1 and T3 constitutes a coil 2 having the smallest coil length. A coil portion between the terminals T1 and T4 constitutes a coil 3 having an intermediate coil length. Therefore, the inductance L of the detection coil 63A can be varied by varying the length of the coil portions.

In the example shown in FIG. 10B, the detection coil 63A is formed by winding a wire or a conductive material ln in a spiral fashion by a single row and N-layers. As shown in FIG. 10B, the coil wound in a spiral fashion has an inner circumferential end and an outer circumferential end which are connected respectively to terminals T1, T2, and intermediate points which are connected respectively to terminals T3, T4. A coil portion between the terminals T1 and T2 constitutes a coil 1 having the largest coil length. A coil portion between the terminals T1 and T3 constitutes a coil 2 having the smallest coil length. A coil portion between the terminals T1 and T4 constitutes a coil 3 having an intermediate coil length. Therefore, the inductance L of the detection coil 63A can be varied by varying the length of the coil portions.

In the examples shown in FIGS. 10A and 10B, the methods of varying the inductance are applied to the inner detection coil 63A. Such methods of varying the inductance shown in FIGS. 10A and 10B are applicable to the outer detection coil 63B and also to the exciting coils 62A, 62B and the dummy coils 64A, 64B.

Figure 11A:
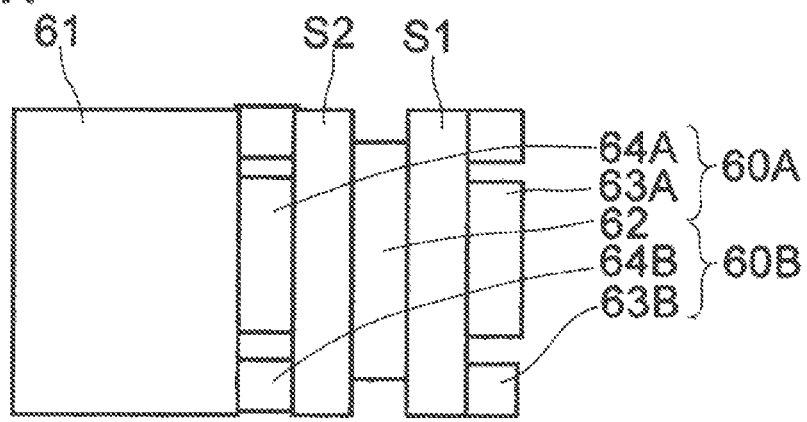
FIG. 11A is a schematic view showing another structural example of sensor coils used in the eddy current sensor of the present invention.
Figure 11B:
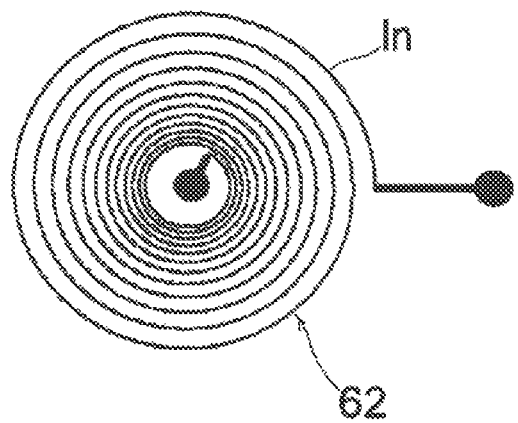
FIG. 11B is a schematic plan view of an exciting coil of the sensor coils shown in FIG. 11A.

FIG. 11A is a schematic view showing another structural example of the sensor coils used in the eddy current sensor according to the present invention. FIG. 11B is a schematic plan view of the exciting coil of the sensor coils shown in FIG. 11A. In FIG. 11A, the coils are schematically shown with the wires or conductive material being omitted from illustration.

As shown in FIG. 11A, the eddy current sensor 50 comprises two sensor coils 60A, 60B which share a common exciting coil 62. The inner sensor coil 60A comprises a detection coil 63A, an exciting coil 62 and a dummy coil 64A, and the outer sensor coil 60B comprises a detection coil 63B, an exciting coil 62 and a dummy coil 64B. The two detection coils 63A, 63B are spaced from each other such that the outer detection coil 63B surrounds the inner detection coil 63A. The two dummy coils 64A, 64B are spaced from each other such that the outer dummy coil 64B surrounds the inner dummy coil 64A.

FIG. 11B is a view showing the exciting coil 62. As shown in FIG. 11B, the exciting coil 62 comprises a single coil formed by winding a wire or a conductive material ln radially in a spiral fashion by a single row and N-layers. The detection coils 63A, 63B and the dummy coils 64A, 64B are of the same configuration as the coils shown in FIGS. 4B and 4C.

Figure 12A:
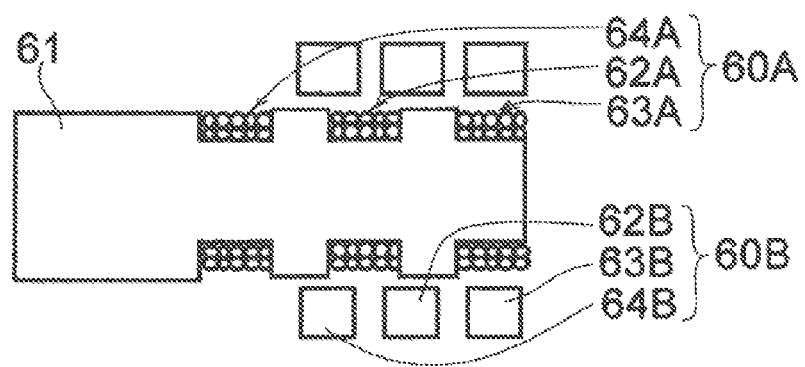
FIGS. 12A and 12B are views showing other structural examples of sensor coils used in the eddy current sensor of the present invention, FIG. 12A being a schematic view showing an example in which an inner sensor coil comprises coils wound in a solenoidal fashion and an outer sensor coil comprises coils wound in a spiral fashion, and FIG. 12B being a schematic view showing an example in which an inner sensor coil comprises coils wound in a spiral fashion and an outer sensor coil comprises coils wound in a solenoidal fashion.
Figure 12B:
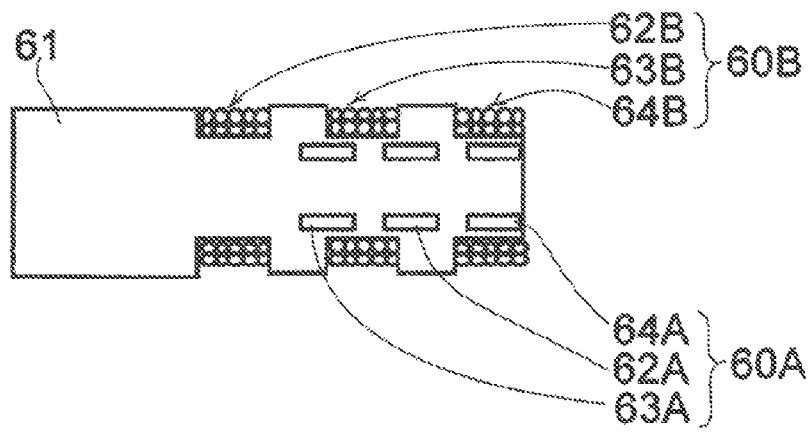

FIGS. 12A and 12B are views showing other structural examples of the sensor coils used in the eddy current sensor according to the present invention. FIG. 12A is a schematic view showing an example in which the inner sensor coil 60A comprises coils wound in a solenoidal fashion and the outer sensor coil 60B comprises coils wound in a spiral fashion. In FIG. 12A, the outer sensor coil 60B is schematically shown with the wires or conductive material being omitted from illustration.

As shown in FIG. 12A, each of the three coils 62A, 63A and 64A in the inner sensor coil 60A comprises a coil formed by winding a wire or a conductive material ln in a solenoidal fashion by N-rows and M-layers around the circumference of the bobbin 61, the row being defined as a direction perpendicular to a surface having a metal film (or conductive film) of the semiconductor wafer (substrate) W and the layer being defined as a direction parallel to the surface having the metal film (or conductive film) of the semiconductor wafer (substrate) W. N, M are integers not less than 2, and each of the coils has 5 rows and 2 layers in the example shown in FIG. 12A. The central coil 62A is an exciting coil, the coil 63A disposed at the metal film (or conductive film) side of the exciting coil 62A is a detection coil, and the coil 64A disposed at the opposite side of the detection coils 63A with respect to the exciting coil 62A is a dummy coil.

The outer sensor coil 60B comprises three coils 62B, 63B and 64B which are not wound around the bobbin 61. Each of the three coils 62B, 63B and 64B in the sensor coil 60B comprises a coil formed by winding a wire or a conductive material ln in a spiral fashion by a single row and N-layers, the row being defined as a direction perpendicular to a surface having a metal film (or conductive film) of the semiconductor wafer (substrate) W and the layer being defined as a direction parallel to the surface having the metal film (or conductive film) of the semiconductor wafer (substrate) W. N is integer not less than 2, and for example, if the number of the turns is more than or equal to the conventional one, N is not less than 11. The central coil 62B is an exciting coil, the coil 63B disposed at the metal film (or conductive film) side of the exciting coil 62B is a detection coil, and the coil 64B disposed at the opposite side of the detecting coil 63B with respect to the exciting coil 62A is a dummy coil. In FIG. 12A, no spacers, but only spaces, are provided between the exciting coil 62B and the detection coil 63B and between the exciting coil 62B and the dummy coil 64B.

FIG. 12B is a schematic view showing an example in which the inner sensor coil 60A comprises coils wound in a spiral fashion and the outer sensor coil 60B comprises coils wound in a solenoidal fashion. The inner and outer sensor coils shown in FIG. 12B are reversed in the inner and outer array from those shown in FIG. 12A. That is, the inner sensor coils shown in FIG. 12A correspond to the outer sensor coils shown in FIG. 12B and the outer sensor coils shown in FIG. 12A correspond to the inner sensor coils shown in FIG. 12B. Specifically, as shown in FIG. 12B, each of three coils 62A, 63A, 64A in the inner sensor coil 60A comprises a coil formed by winding a wire or a conductive material ln in a spiral fashion by a single rows and N-layers, and each of three coils 62B, 63B, 64B in the outer sensor coil 60B comprises a coil formed by winding a wire or a conductive material ln in a solenoidal fashion by N-rows and M-layers.

Figure 13:
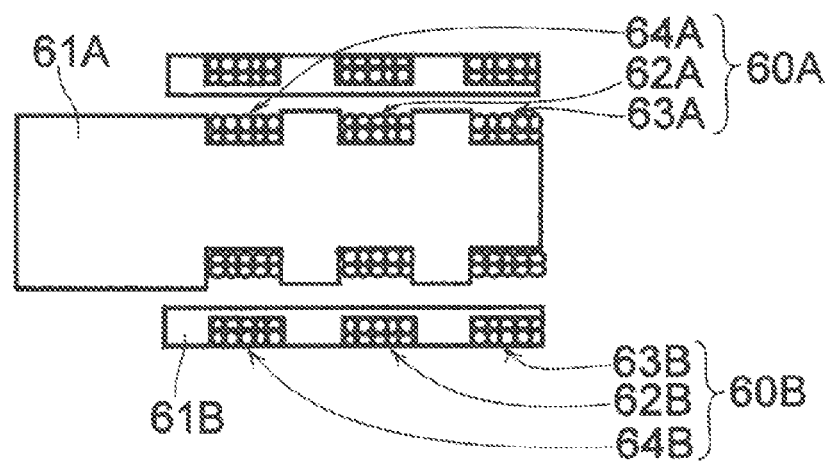
FIG. 13 is a schematic view showing another structural example of sensor coils used in the eddy current sensor of the present invention, and showing an example in which each coil in an inner sensor coil and an outer sensor coil comprises a coil wound in a solenoidal fashion.

FIG. 13 is a schematic view showing another structural example of the sensor coils used in the eddy current sensor of the present invention. FIG. 13 is a schematic view showing an example in which each coil in the inner sensor coil 60A and the outer sensor coil 60B comprises a coil wound in a solenoidal fashion. As shown in FIG. 13, each of the three coils 62A, 63A and 64A in the inner sensor coil 60A comprises a coil formed by winding a wire or a conductive material ln in a solenoidal fashion by N-rows and M-layers around the circumference of a bobbin 61A, the row being defined as a direction perpendicular to a surface having a metal film (or conductive film) of the semiconductor wafer (substrate) W and the layer being defined as a direction parallel to the surface having the metal film (or conductive film) of the semiconductor wafer (substrate) W. N, M are integers not less than 2, and each of the coils has 5 rows and 2 layers in the example shown in FIG. 13. The central coil 62A is an exciting coil, the coil 63A disposed at a metal film (or conductive film) side of the exciting coil 62A is a detection coil, and the coil 64A disposed at the opposite side of the detection coils 63A with respect to the exciting coil 62A is a dummy coil.

Each of the three coils 62B, 63B and 64B in the outer sensor coil 60B comprises a coil formed by winding a wire or a conductive material ln in a solenoidal fashion by N-rows and M-layers around the circumference of a hollow bobbin 61B, the row being defined as a direction perpendicular to a surface having a metal film (or conductive film) of the semiconductor wafer (substrate) W and the layer being defined as a direction parallel to the surface having the metal film (or conductive film) of the semiconductor wafer (substrate) W. N, M are integers not less than 2, and each of the coils has 5 rows and 2 layers in the example shown in FIG. 13. The central coil 62B is an exciting coil, the coil 63B disposed at a metal film (or conductive film) side of the exciting coil 62B is a detection coil, and the coil 64B disposed at the opposite side of the detection coils 63B with respect to the exciting coil 62B is a dummy coil.

As shown in FIGS. 4 through 13, the eddy current sensor 50 according to the present invention comprises a plurality of sensor coils 60A, 60B having different outer coil diameters, and spaced from each other such that the outer sensor coil 60B surrounds the inner sensor coil 60B.

With the eddy current sensor 50 according to the present invention, the outer coil diameters of the detection coil 63A, the exciting coil 62A, and the dummy coil 64A of the inner sensor coil 60A are smaller than the outer coil diameters of the detection coil 63B, the exciting coil 62B, and the dummy coil 64B of the outer sensor coil 60B. For example, a comparison between the inner detection coil 63A and the outer detection coil 63B of the eddy current sensor 50 shown in FIGS. 4B and 4C indicates that the inner detection coil 63A has an outer coil diameter D1 and the outer detection coil 63B has an outer coil diameter D2, with the outer coil diameters D1, D2 being configured to have a relation of D2>>D1. Since the outer coil diameter D1 of the inner detection coil 63A is smaller, the inner detection coil 63A is capable of detecting an eddy current in a small area (first area) of a target metal film or conductive film. The outer detection coil 63B having the larger outer coil diameter D2 is capable of detecting an eddy current in a large area (second area) including the small area (first area) measured by the inner detection coil 63A.

As shown in FIG. 2, the eddy current sensor 50 scans the surface (surface being polished) of the semiconductor wafer (substrate) W each time the polishing table 100 makes one revolution. During this time, the inner detection coil 63A and the outer detection coil 63B scan the surface being polished of the semiconductor wafer W on the same locus. Therefore, the inner detection coil 63A and the outer detection coil 63B can measure the metal film or conductive film of the semiconductor wafer W on the same locus simultaneously and continuously. Specifically, on the same locus, the inner detection coil 63A can measure the metal film or conductive film by detecting an eddy current in the small area (first area) of the target metal film or conductive film, and the outer detection coil 63B can measure the metal film or conductive film by detecting an eddy current in the large area (second area) including the small area (first area).

As shown in FIG. 4B, corresponding to the inner and outer detection coils 63A, 63B, the inner exciting coil 62A has an outer coil diameter D1 and the outer exciting coil 62B has an outer coil diameter D2, with the outside diameters D1, D2 being configured to have a relation of D2>>D1. Since the outer coil diameters D1, D2 of the inner and outer exciting coils 62A, 62B are selected as described above, the inner exciting coil 62A is capable of generating an eddy current in a small area (first area) of a target metal film or conductive film, and the outer exciting coil 62B is capable of generating an eddy current in a large area (second area) including the small area (first area). Although the outer coil diameters of the exciting coils 62A, 62B are described as being the same as the outer coil diameters of the detection coils 63A, 63B, the outer coil diameters of the exciting coils 62A, 62B may be different from the outer coil diameters of the detection coils 63A, 63B.

As described above, the eddy current sensor 50 according to the present invention comprises the inner sensor coil 60A which comprises the exciting coil 62A, the detection coil 63A and the dummy coil 64A, and the outer sensor coil 60B which is disposed so as to surround the inner sensor coil 60A and comprises the exciting coil 62B, the detection coil 63B and the dummy coil 64B. The inner sensor coil 60A serves as a sensor having a high sensitivity, and it is capable of detecting a metal film even when the target metal film becomes thin or the remaining area of the metal film becomes small. Therefore, the inner sensor coil 60A can detect detailed distribution state of the remaining film on the surface, being polished, of the semiconductor wafer (substrate) W, and can also detect the thin film at the edge area of the semiconductor wafer W. The outer sensor coil 60B serves as a sensor having a low sensitivity, and it is capable of detecting the remaining film accurately over the entire surface, being polished, of the semiconductor wafer (substrate) W, and detecting the polishing end point stably. Furthermore, since the inner sensor coil 60A and the outer sensor coil 60B respond to a metal film or conductive film simultaneously on the same locus and provide respective outputs, the metal film (or conductive film) can be detected with high accuracy by comparing these output values.

Modifications of the eddy current sensor 50 according to the present invention will be described below.

In the embodiments shown in FIGS. 4 through 13, the eddy current sensor 50 has been described which includes the inner and outer sensor coils 60A, 60B having different outer coil diameters and disposed separately from each other such that the outer sensor coil 60B surrounds the inner sensor coil 60A. However, the eddy current sensor 50 may be configured such that coils of the same kind in the sensor coils 60A, 60B overlap each other partly.

Figure 14:
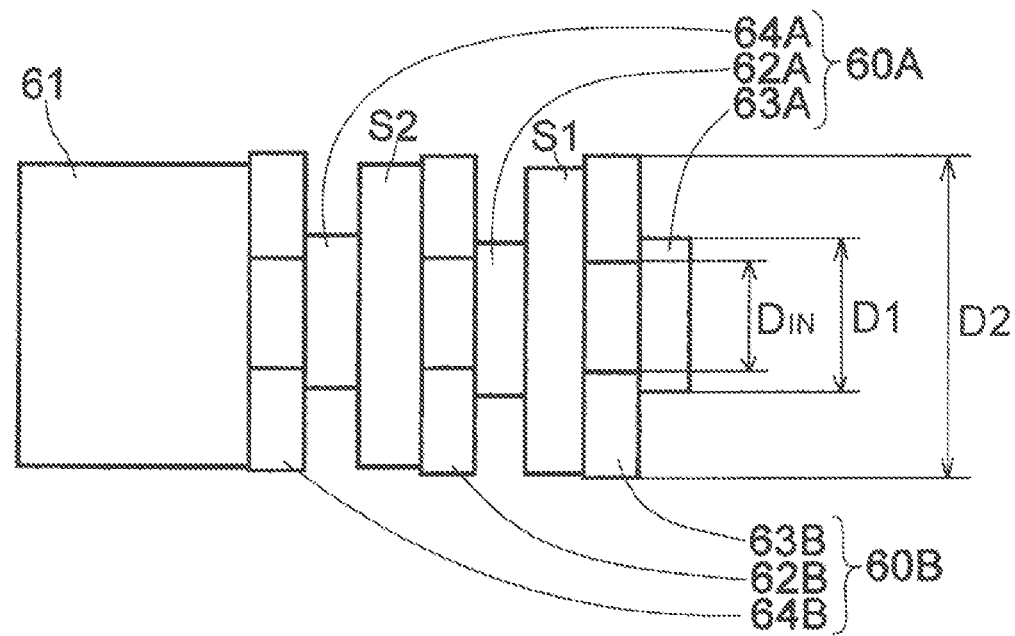
FIG. 14 is a schematic view showing an embodiment in which sensor coils have coils of the same kind that are disposed in overlapping positions.

FIG. 14 is a schematic view showing a structural example in which sensor coils 60A, 60B have coils of the same kind that are disposed in overlapping positions. As shown in FIG. 14, an eddy current sensor 50 according to the present embodiment comprises two sensor coils 60A, 60B. The sensor coil 60A comprises three coils 62A, 63A, 64A which are not wound around a bobbin 61. Each of the three coils 62A, 63A and 64A in the sensor coil 60A comprises a coil formed by winding a wire or a conductive material ln in a spiral fashion by a single row and N-layers, the row being defined as a direction perpendicular to the semiconductor wafer (substrate) W and the layer being defined as a direction parallel to the semiconductor wafer (substrate) W.

The outer sensor coil 60B comprises three coils 62B, 63B, 64B which are not wound around the bobbin 61. Each of the three coils 62B, 63B and 64B in the sensor coil 60B comprises a coil formed by winding a wire or a conductive material ln in a spiral fashion by a single row and N-layers, the row being defined as a direction perpendicular to the semiconductor wafer (substrate) W and the layer being defined as a direction parallel to the semiconductor wafer (substrate) W.

As shown in FIG. 14, the outer coil diameter D1 of the detection coil 63A is larger than the inner coil diameter $D_{IN}$ of the detection coil 63B. The two detection coils 63A, 63B overlap each other partly in the row direction. Similarly, the outer coil diameter of the exciting coil 62A is larger than the inner coil diameter of the exciting coil 62B. The two exciting coils 62A, 62B overlap each other partly in the row direction. The outer coil diameter of the dummy coil 64A is also larger than the inner coil diameter of the dummy coil 64B. The two dummy coils 64A, 64B overlap each other partly in the row direction.

With the eddy current sensor 50 shown in FIG. 14, the outer coil diameters of the detection coil 63A, the exciting coil 62A, and the dummy coil 64A of the sensor coil 60A are smaller than the outer coil diameters of the detection coil 63B, the exciting coil 62B, and the dummy coil 64B of the sensor coil 60B. For example, a comparison between the detection coil 63A and the detection coil 63B of the eddy current sensor 50 shown in FIG. 14 indicates that the detection coil 63A has an outer coil diameter D1 and the detection coil 63B has an outer coil diameter D2, with the outer coil diameters D1, D2 being configured to have a relation of D2>>D1. Since the outer coil diameter D1 of the detection coil 63A is small, the detection coil 63A is capable of detecting an eddy current in a small area (first area) of a target metal film or conductive film. The detection coil 63B having a large outer coil diameter D2 is capable of detecting an eddy current in a large area (second area) including the area (first area) measured by the detection coil 63A.

Corresponding to the detection coils 63A, 63B, the exciting coil 62A has an outer coil diameter D1 and the exciting coil 62B has an outer coil diameter D2, with the outer coil diameters D1, D2 being configured to have a relation of D2>>D1. Since the outer coil diameters D1, D2 of the exciting coils 62A, 62B are selected as described above, the exciting coil 62A is capable of generating an eddy current in a small area (first area) of a target metal film or conductive film, and the exciting coil 62B is capable of generating an eddy current in a large area (second area) including the small area (first area). Although the outer coil diameters of the exciting coils 62A, 62B are described as being the same as the outer coil diameters of the detection coils 63A, 63B, the outer coil diameters of the exciting coils 62A, 62B may be different from the outer coil diameters of the detection coils 63A, 63B, respectively.

A spacer S1 is interposed between the detection coil 63B and the exciting coil 62A to keep a distance between the detection coil 63B and the exciting coil 62A constant. A spacer S2 is interposed between the exciting coil 62B and the dummy coil 64A to keep a distance between the exciting coil 62B and the dummy coil 64A constant. A bobbin 61 is disposed adjacent to the dummy coil 64B. As long as a distance is provided between the detection coil 63B and the exciting coil 62A and between the exciting coil 62B and the dummy coil 64A, only space is sufficient without providing a spacer.

Next, specific examples in which m number of coils having a single row and N-layers are connected in series in the eddy current sensor of the present invention, which includes the sensor coil having a large outer diameter and the sensor coil having a small outer diameter as shown in FIGS. 4 through 14 will be described below with reference to FIGS. 15A, 15B and 15C.

Figure 15A:
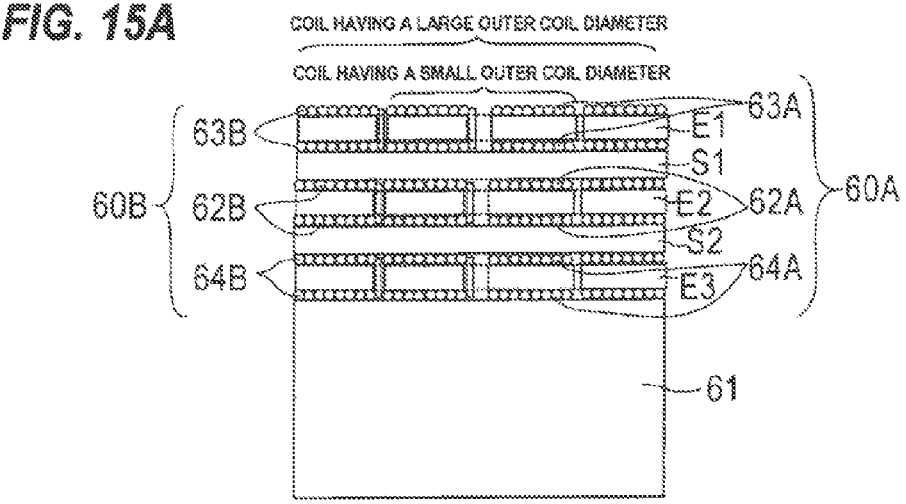
FIG. 15A is a schematic view showing an embodiment in which two coils having a single row and N-layers are connected in series.

FIG. 15A is a schematic view showing an example in which a coil having a large outer coil diameter surrounds a coil having a small outer coil diameter, and the two coils having a large outer coil diameter or two coils having a small outer coil diameter are connected in series. Specifically, as shown in FIG. 15A, an inner sensor coil 60A comprises a detection coil 63A, an exciting coil 62A, and a dummy coil 64A. Each of the detection coil 63A, the exciting coil 62A, and the dummy coil 64A comprises two coils connected in series to each other, each coil being formed by winding a wire or a conductive material ln in a spiral fashion by a single row and N-layers. An outer sensor coil 60B comprises a detection coil 63B, an exciting coil 62B, and a dummy coil 64B. Each of the detection coil 63B, the exciting coil 62B, and the dummy coil 64B comprises two coils connected in series to each other, each coil being formed by winding a wire or a conductive material ln in a spiral fashion by a single row and N-layers. When the two coils are connected in series to each other, they may be connected at their inner sides or outer sides. In the case where two coils, each formed in a single row and N-layers, are connected in series, if the coils are held in contact with each other, then their capacitance component increases. Accordingly, the two coils, each formed in a single row and N-layers are arrayed in the row direction, i.e., a direction perpendicular to the substrate, with a gap provided between adjacent coils, and materials E1, E2, E3 having a low-dielectric constant are interposed respectively in the gaps. As is the case with the example shown in FIG. 4B, spacers S1 and S2 are interposed respectively between the detection coil and the exciting coil and between the exciting coil and the dummy coil.

Figure 15B:
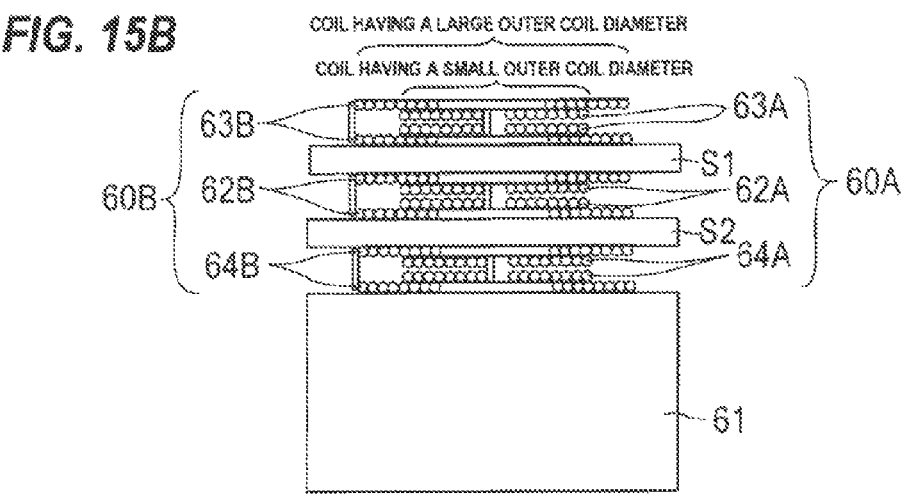
FIG. 15B is a schematic view showing an embodiment in which two coils having a single row and N-layers are connected in series.

FIG. 15B is a schematic view showing an example in which coils having a large outer coil diameter sandwich a coil having a small outer coil diameter in a direction perpendicular to the surface of a semiconductor wafer (substrate) W on which a metal film is formed, and the two coils having a large outer coil diameter or two coils having a small outer coil diameter are connected in series. Specifically, as shown in FIG. 15B, an inner sensor coil 60A comprises a detection coil 63A, an exciting coil 62A, and a dummy coil 64A. Each of the detection coil 63A, the exciting coil 62A, and the dummy coil 64A comprises two coils connected in series to each other, each coil being formed by winding a wire or a conductive material ln in a spiral fashion by a single row and N-layers. An outer sensor coil 60B comprises a detection coil 63B, an exciting coil 62B, and a dummy coil 64B. Each of the detection coil 63B, the exciting coil 62B, and the dummy coil 64B comprises two coils connected in series to each other, each coil being formed by winding wire or a conductive material ln in a spiral fashion by a single row and N-layers. When the two coils are connected in series to each other, they may be connected at their inner sides or outer sides. As is the case with the example shown in FIG. 15A, spacers S1 and S2 are interposed respectively between the detection coil and the exciting coil and between the exciting coil and the dummy coil. Although not shown, a gap may be provided between the adjacent coils having a small outer coil diameter, and a material having a low-dielectric constant may be interposed in the gap, as is the case with the example shown in FIG. 15A.

Figure 15C:
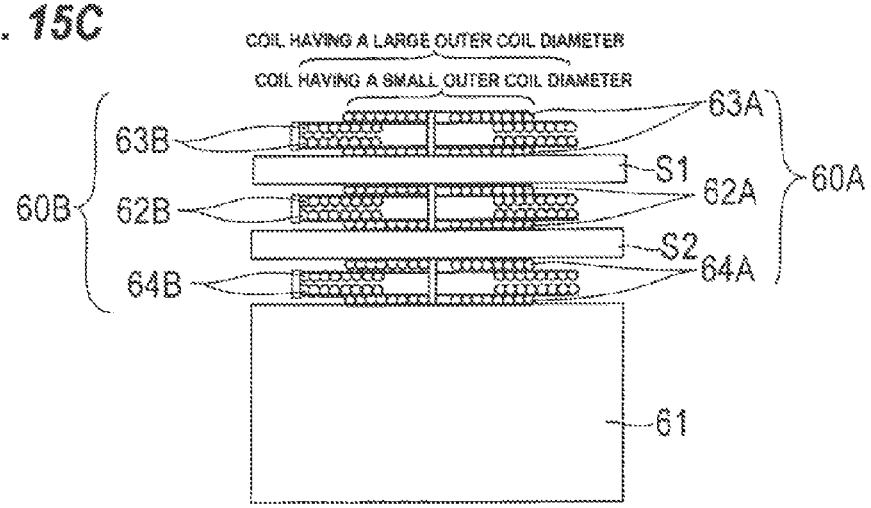
FIG. 15C is a schematic view showing an embodiment in which two coils having a single row and N-layers are connected in series.

FIG. 15C is a schematic view showing an example in which coils having a small outer coil diameter sandwich a coil having a large outer coil diameter in a direction perpendicular to the surface of a semiconductor wafer (substrate) W on which a metal film is formed, and the two coils having a small outer coil diameter or two coils having a large outer coil diameter are connected in series. Specifically, as shown in FIG. 15C, an inner sensor coil 60A comprises a detection coil 63A, an exciting coil 62A, and a dummy coil 64A. Each of the detection coil 63A, the exciting coil 62A, and the dummy coil 64A comprises two coils connected in series to each other, each coil being formed by winding a wire or a conductive material ln in a spiral fashion by a single row and N-layers. An outer sensor coil 60B comprises a detection coil 63B, an exciting coil 62B, and a dummy coil 64B. Each of the detection coil 63B, the exciting coil 62B, and the dummy coil 64B comprises two coils connected in series to each other, each coil being formed by winding a wire or a conductive material ln in a spiral fashion by a single row and N-layers. When the two coils are connected in series to each other, they may be connected at their inner sides or outer sides. As is the case with the example shown in FIG. 15A, spacers S1 and S2 are interposed respectively between the detection coil and the exciting coil and between the exciting coil and the dummy coil. Although not shown, a gap may be provided between the adjacent coils having a large outer coil diameter, and a material having a low-dielectric constant may be interposed in the gap, as is the case with the example shown in FIG. 15A.

Figure 16A:
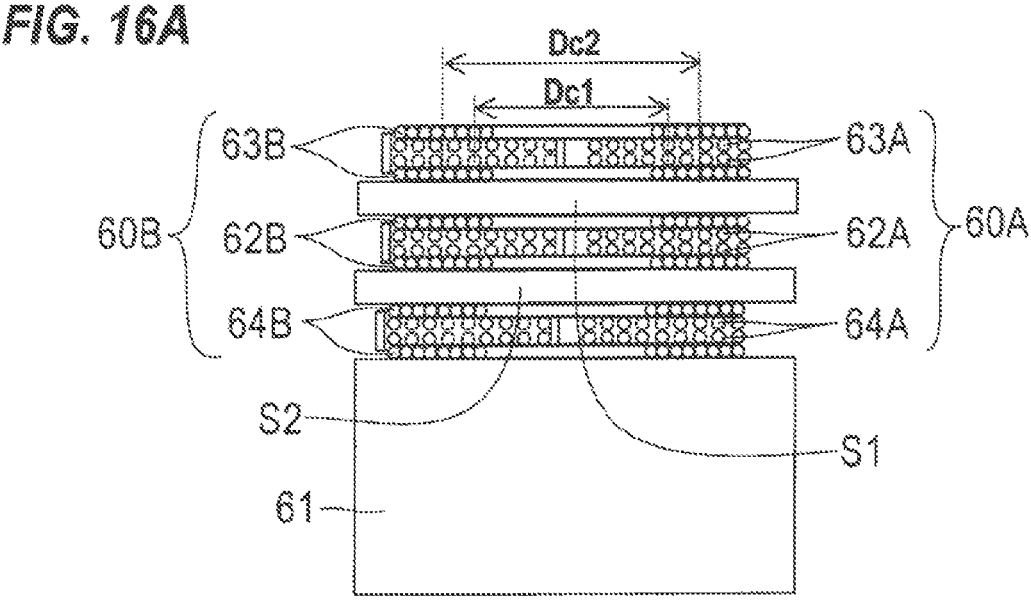
FIG. 16A is a schematic view showing an embodiment in which two coils differ in a median coil diameter and are connected in series to each other.
Figure 16B:
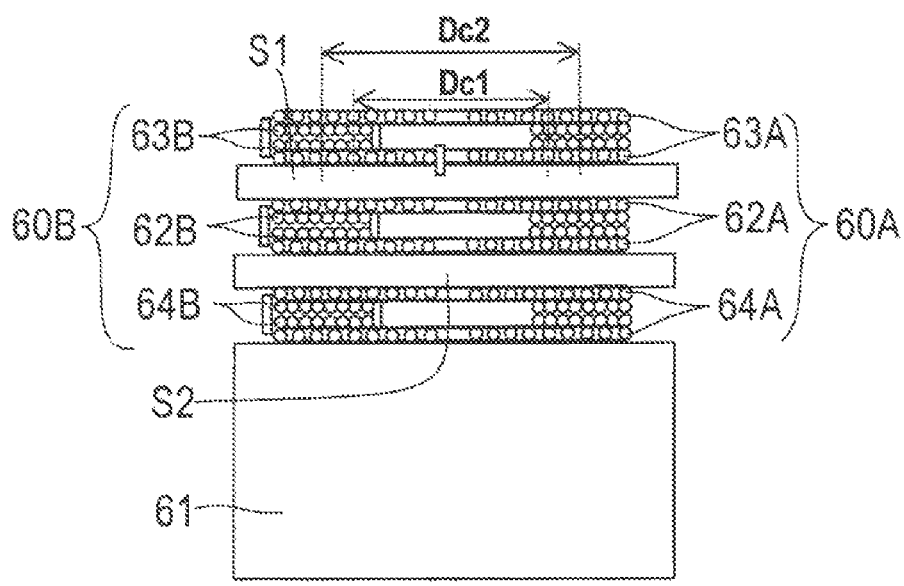
FIG. 16B is a schematic view showing an embodiment in which two coils differ in a median coil diameter and are connected in series to each other.

FIGS. 4 through 15 show combinations of coils having a large outer coil diameter and coils having a small outer coil diameter. The present invention also covers combinations of sensor coils having a large median coil diameter and sensor coils having a small median coil diameter. FIGS. 16A and 16B are schematic views showing examples in which two coils differ in a median coil diameter and are connected in series to each other. In FIGS. 16A and 16B, a median coil diameter is defined as an arithmetic average of an inner diameter and an outer diameter of a coil, and a coil having a large median coil diameter is referred to as an outer coil and a coil having a small median coil diameter is referred to as an inner coil.

In the examples shown in FIGS. 16A and 16B, an outer sensor coil 60B comprises a detection coil 63B, an exciting coil 62B, and a dummy coil 64B, and an inner sensor coil 60A comprises a detection coil 63A, an exciting coil 62A, and a dummy coil 64A. The median coil diameters of the detection coil 63B, the exciting coil 62B, and the dummy coil 64B are larger than the median coil diameters of the detection coil 63A, the exciting coil 62A, and the dummy coil 64A. Each of the detection coils 63A, 63B, the exciting coils 62A, 62B, and the dummy coils 64A, 64B comprises two coils connected in series to each other, each coil being formed by winding wire or a conductive material ln in a spiral fashion by a single row and N-layers.

A comparison between the detection coil 63A and the detection coil 63B of the eddy current sensor 50 shown in FIGS. 16A and 16B indicates that the detection coil 63A has a median coil diameter Dc1 and the detection coil 63B has a median coil diameter Dc2, the median coil diameters Dc1, Dc2 being configured to have a relation of Dc2>Dc1. The detection coil 63A having a small median coil diameter Dc1 is capable of detecting an eddy current in a small area (first area) of a target metal film or a conductive film. The detection coil 63B having a large median coil diameter Dc2 is capable of detecting an eddy current in a large area (second area) including the area (first area) measured by the detection coil 63A.

Corresponding to the detection coils 63A, 63B, the exciting coil 62A has a median coil diameter Dc1 and the exciting coil 62B has a median coil diameter Dc2, with the median coil diameters Dc1, Dc2 being configured to have a relation of Dc2>Dc1. Since the median coil diameters Dc1, Dc2 of the exciting coils 62A, 62B are selected as described above, the exciting coil 62A is capable of generating an eddy current in a small area (first area) of a target metal film or a conductive film, and the exciting coil 62B is capable of generating an eddy current in a large area (second area) including the small area (first area). Although the median coil diameters of the exciting coils 62A, 62B are described as being the same as the median coil diameters of the detection coils 63A, 63B, the median coil diameters of the exciting coils 62A, 62B may be different from the median coil diameters of the detection coils 63A, 63B. The dummy coils 64A, 64B have respective median coil diameters which are the same as the median coil diameters of the detection coils 63A, 63B. As is the case with the example shown in FIG. 4B, spacers S1 and S2 are interposed respectively between the detection coil and the exciting coil and between the exciting coil and the dummy coil. Although not shown, a gap may be provided between the adjacent coils, and a material having a low-dielectric constant may be interposed in the gap, as is the case with the example shown in FIG. 15A.

Figure 17:
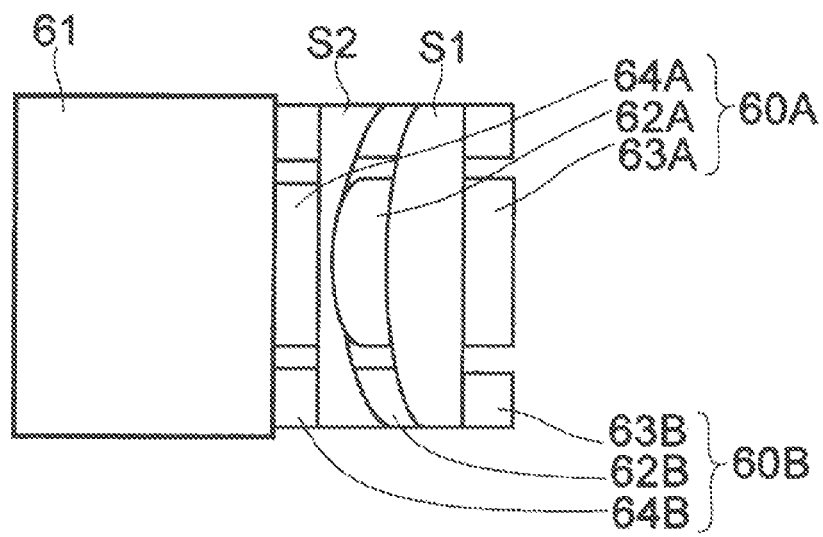
FIG. 17 is a schematic view showing an example in which exciting coils among respective coils of sensor coils are formed into the form of concave sphere.

FIG. 17 is a schematic view showing an example in which exciting coils 62A, 62B among respective coils 62A, 62B, 63A, 63B, 64A, 64B of sensor coils 60A, 60B are formed into the form of concave sphere. As shown in FIG. 17, each of the exciting coils 62A, 62B comprises a coil formed by winding a wire or an conductive material such that the coil is curved in the form of concave sphere so as to be dented toward the dummy coil side at a radially inner side and to be closer to the detection coil side toward a radially outer side. The sensor coil wound in a spiral fashion can vary its sensitivity by varying an exciting magnetic field. Therefore, as shown in FIG. 17, since the exciting coils 62A, 62B are curved in the form of concave sphere, the exciting magnetic field can converge on the central areas and the sensor sensitivity can be improved.

Figure 18:
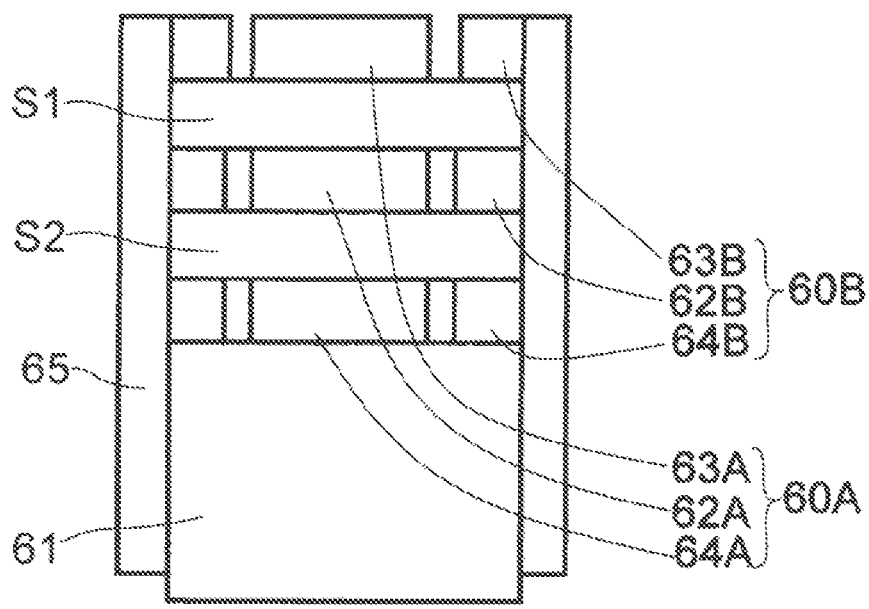
FIG. 18 is a schematic view showing an example in which a tubular member made of a material having a high-magnetic permeability is disposed around the sensor coils shown in FIG. 4B.

FIG. 18 is a schematic view showing an example in which a tubular member made of a material having a high-magnetic permeability is disposed around the sensor coils shown in FIG. 4B. As shown in FIG. 18, a bobbin 61 and three outer coils 62B, 63B, 64B in the sensor coils 60A, 60B are housed in a tubular member 65 made of a material having a high-magnetic permeability. The tubular member 65 may be made of a material having a high-magnetic permeability, for example, ferrite, amorphous, permalloy, supermalloy, or mumetal so that the relative permeability μ is 50. Thus, the tubular member 65 can pass 50 times as much magnetic flux as in the case where the environment surrounding the sensor coil is air. In other words, the tubular member 65 can pass an equivalent magnetic flux with one-fiftieth in its thickness compared to the case where an electrically-insulating material such as a ceramic material is disposed around the sensor coil.

As shown in FIG. 18, since the tubular member 65 made of a material having a high-magnetic permeability is disposed around the sensor coils, even when the polishing table 100 is made of a conductive material such as stainless steel (SUS) material, a current is supplied to the exciting coils 62A, 62B of the sensor coils 60A, 60B disposed in the tubular member 65 to generate a magnetic flux. With such structure, an eddy current is not generated in the polishing table by the magnetic flux, and paths of the magnetic flux (magnetic circuits), which are required for measurement, are not reduced. Accordingly, it is possible to maintain the paths so as to effectively generate an eddy current in the metal film on the semiconductor wafer W. Specifically, the tubular member 65 serves as a path to prevent the magnetic flux generated by the exciting coils 62A, 62B of the sensor coils 60A, 60B from passing through the conductive base material of the polishing table 100 and to expand the magnetic flux into the detection space on the semiconductor wafer W. Thus, the magnetic flux can generate a large amount of eddy current in the metal film (or conductive film) mf to be measured. Therefore, even in the case of the polishing table 100 made of a conductive material such as stainless steel (SUS), it is possible to maintain the same sensitivity for detecting the eddy current as in the case of the polishing table 100 made of a ceramic material (insulating material) such as SiC.

The structures in which inner and outer detection coils are spaced from each other such that the outer detection coil surrounds the inner detection coil, each of the inner and outer detection coils being formed by winding by a single row and N-layers in a spiral fashion, in a polygonal shape, in an elliptical shape or the like, as shown in FIGS. 4 through 9, are applicable to a sensor which can detect the polishing end point based on a change in the exciting frequencies, and is configured to have a Colpitts circuit comprising detection coils and capacitors connected to each other in parallel for obtaining exciting function and detecting function.

According to the embodiments shown in FIGS. 4 through 18, coils are disposed in radially inner and outer positions in the respective detection coils, exciting coils, and dummy coils. However, three or more detection coils, exciting coils, and dummy coils may be disposed concentrically or substantially concentrically from radially inner side toward radially outer side.

Figure 19:
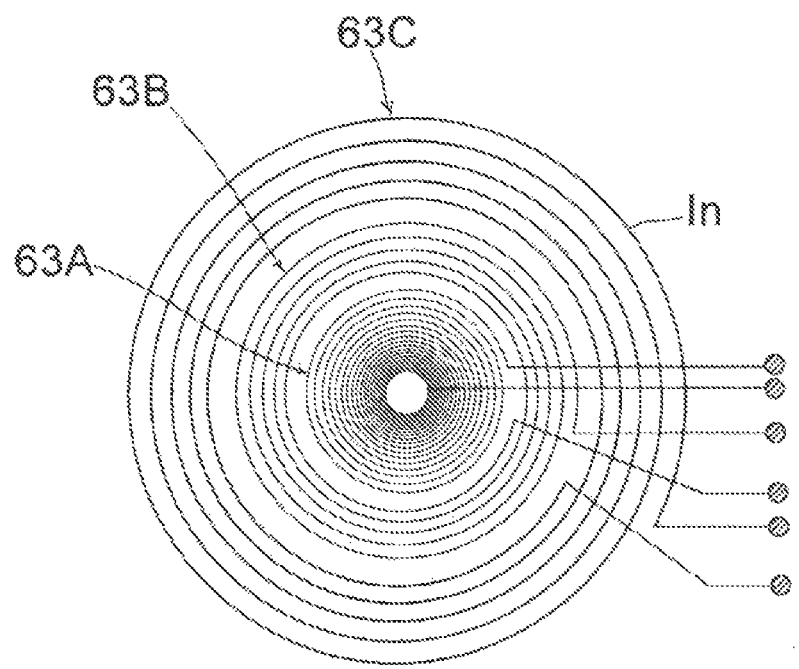
FIG. 19 is a schematic view showing an example in which three detection coils wound in a spiral fashion are disposed concentrically in respective positions.

FIG. 19 is a schematic view showing an example in which three detection coils 63A, 63B, 63C wound in a spiral fashion are disposed concentrically in respective positions. Each of the three detection coils 63A, 63B, 63C comprises a coil formed by winding a wire or a conductive material ln in a spiral fashion by a single row and N-layers. The three detection coils 63A, 63B, 63C may be integrally formed by a printed wiring process.

As shown in FIG. 19, the eddy current sensor 50 has the three detection coils 63A, 63B, 63C that are disposed concentrically. The detection coil 63A which is disposed in a radially innermost position has an outer coil diameter D1, the detection coil 63B which is disposed in an intermediate position has an outer coil diameter D2, and the detection coil 63C which is disposed in a radially outermost position has an outer coil diameter D3, the outer coil diameters D1, D2, D3 being configured to have a relation of D1<D2<D3. The detection coil 63A having the smallest outer coil diameter D1, which is disposed in the radially innermost position, can detect an eddy current in a small area (first area) of a target metal film or a conductive film. The detection coil 63B, which is disposed in the intermediate position, can detect an eddy current in a large area (second area) including the area (first area) measured by the detection coil 63A in the radially innermost position. The detection coil 63C, which is disposed in the radially outermost position, can detect an eddy current in a more larger area (third area) including the area measured by the detection coil 63B in the intermediate position. The three exciting coils and the three dummy coils are of the same structure as the detection coils 63A, 63B, 63C shown in FIG. 19.

FIGS. 20A, 20B and 20C are schematic views showing a circuit configuration of the coils of the sensor coil 60A. FIG. 20A shows only the circuit configuration of the sensor coil 60A comprising the coils 62A, 63A and 64A. The sensor coil 60B comprising the coils 62B, 63B and 64B has the same circuit configuration as the sensor coil 60A, and thus illustration and description of the sensor coil 60B will be omitted.

As shown in FIG. 20A, the coils 62A, 63A and 64A comprise coils wound in a spiral fashion by a single row and N-layers, and the detection coil 63A and the dummy coil 64A are connected in negative-phase to each other.

The detection coil 63A and the dummy coil 64A constitute a negative-phase series circuit whose terminal ends are connected to a resistance bridge circuit 77 including variable registers 76. The exciting coil 62A is connected to the AC signal source 52, and produces an alternating magnetic flux to generate an eddy current in the metal film (or conductive film) mf that is disposed closely to the coil 62A. By adjusting the resistances of the variable resistors 76, an output voltage of the series circuit having the coils 63A and 64A can be adjusted such that the output voltage is zero when no metal film (or conductive film) is present nearby. The variable resistors 76 ($VR_1$, $VR_2$) are connected in parallel to the coils 63A and 64A, and are adjusted to keep signals $L_1$ and $L_3$ in phase with each other. Specifically, in the equivalent circuit of FIG. 20B, the variable resistors $VR_1(=VR_{1-1}+VR_{1-2})$, $VR_2(=VR_{2-1}+VR_{2-2})$ are adjusted to satisfy the following equation:

$$VR_{1-1} \times (VR_{2-2}+j\omega L_3) = VR_{1-2} \times (VR_{2-1}+j\omega L_1) \tag{1}$$

In this manner, as shown in FIG. 20C, the signals $L_1$ and $L_3$ (indicated by the dotted lines) are transformed to have the same phase and the same amplitude as each other as indicated by the solid line.

When the metal film (or conductive film) is present near the detection coil 63A, the magnetic flux produced by the eddy current generated in the metal film (or conductive film) interlinks with the detection coil 63A and the dummy coil 64A. Since the detection coil 63A is positioned closer to the metal film (or conductive film) than the dummy coil 64A, induced voltage of the coils 63A and 64A are brought out of balance, thus enabling the detection of the flux linkage produced by the eddy current flowing through the metal film (or conductive film). A zero point can be adjusted by separating the series circuit having the detection coil 63A and the dummy coil 64A from the exciting coil 62A connected to the AC signal source and by adjusting the balance with use of the resistance bridge circuit. Therefore, the eddy current flowing through the metal film (or conductive film) can be detected from the zero point, and thus the eddy current generated in the metal film (or conductive film) can be detected with an increased sensitivity. Therefore, a magnitude of the eddy current flowing through the metal film (or conductive film) can be detected in a wide dynamic range.

Figure 21:
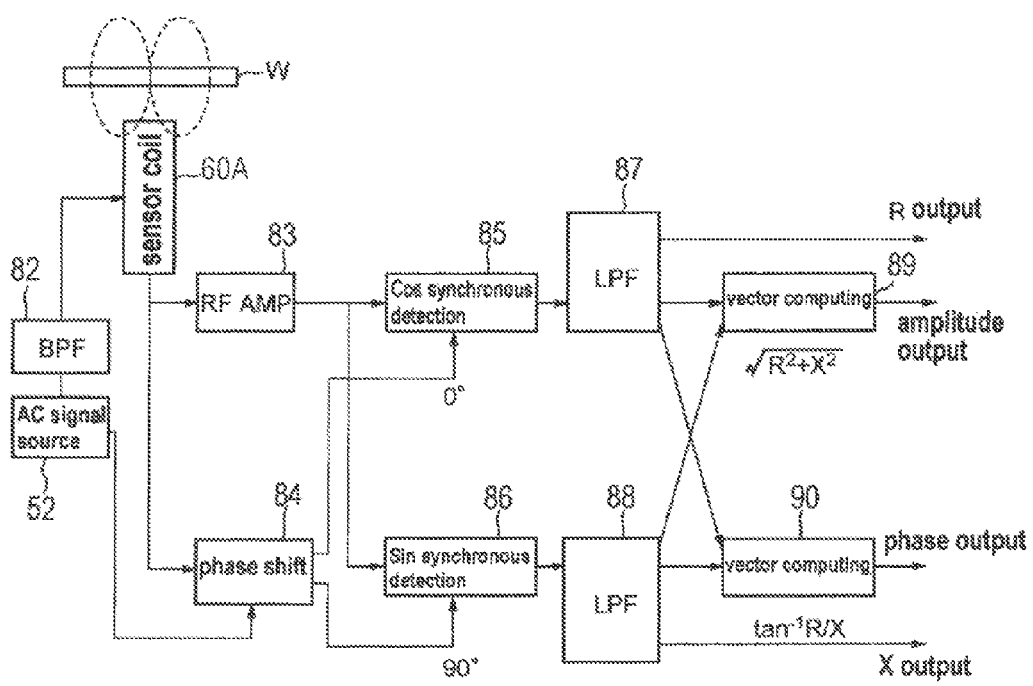
FIG. 21 is a block diagram showing a synchronous detection circuit of the eddy current sensor.

FIG. 21 is a block diagram showing a synchronous detection circuit of the eddy current sensor.

FIG. 21 shows an example of a circuit for measuring the impedance Z as viewed from the AC signal source 52 toward the sensor coil 60A. FIG. 21 shows only the impedance measuring circuit of the sensor coil 60A. The impedance measuring circuit of the sensor coil 60B has the same circuit configuration as the sensor coil 60A, and thus illustration and description of the impedance measuring circuit of the sensor coil 60B will be omitted. The impedance measuring circuit shown in FIG. 21 can extract a resistance component (R), a reactance component (X), an amplitude output (Z), and a phase output ($\tan^{-1}$ R/X), which vary depending on the change in the film thickness.

As described above, the AC signal source 52 supplies an AC signal to the sensor coil 60A disposed closely to the semiconductor wafer W having the metal film (or conductive film) mf to be detected. The AC signal source 52 comprises a fixed-frequency type oscillator such as a crystal quartz oscillator. The AC signal source 52 supplies voltage having a fixed-frequency in the range of 2 MHz to 32 MHz, for example. The AC voltage generated by the AC signal source 52 is sent through a band-pass filter 82 to the sensor coil 60A. A signal detected at the terminal of the sensor coil 60A is supplied through a high-frequency amplifier 83 and a phase shift circuit 84 to a synchronous detection unit comprising a cos synchronous detection circuit 85 and a sin synchronous detection circuit 86. The synchronous detection unit extracts a cos component and a sin component of the detected signal. The oscillation signal generated by the AC signal source 52 is supplied to the phase shift circuit 84 where the oscillation signal is resolved into two signals, i.e. an in-phase component (0°) and an orthogonal component (90°). These two signals are introduced respectively to the cos synchronous detection circuit 85 and the sin synchronous detection circuit 86, thereby performing the above synchronous detection.

The synchronously detected signals are supplied to low-pass filters 87 and 88 which remove unnecessary high-frequency components from the synchronously detected signals, thereby extracting a resistance component (R) as the cos synchronous detection output and a reactance component (X) as the sin synchronous detection output. A vector computing circuit 89 derives an amplitude $(R^2+X^2)^{1/2}$ from the resistance component (R) and the reactance component (X). Further, a vector computing circuit 90 derives a phase output ($\tan^{-1}$ R/X) from the resistance component (R) and the reactance component (X). Here, the measuring device has various types of filters for removing noise components from the sensor signal. These filters have their respective cutoff frequencies. For example, a low-pass filter has a cutoff frequency in the range of 0.1 to 10 Hz for removing noise components which have been mixed into the sensor signal while the semiconductor wafer is being polished. Thus, the metal film (conductive film) to be measured can be measured with high accuracy.

Figure 22A:
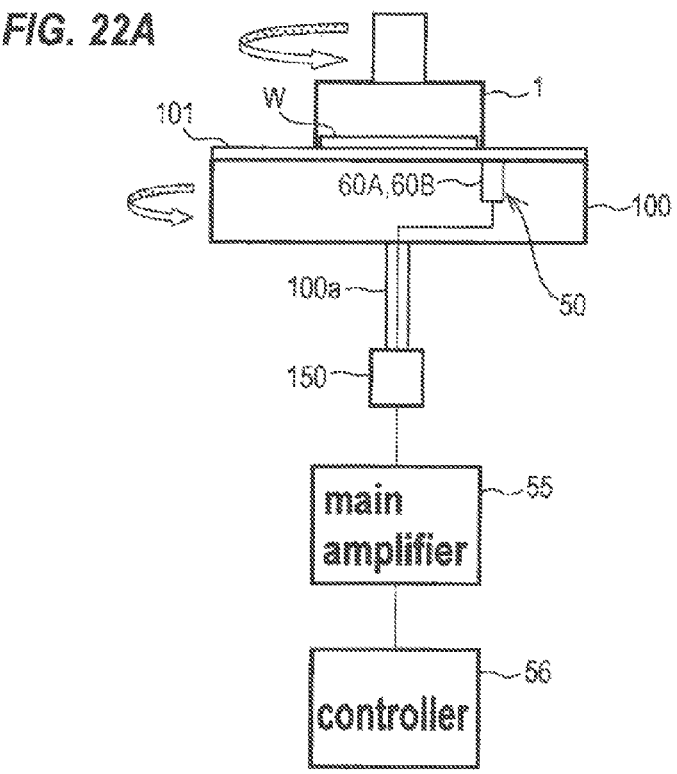
FIGS. 22A and 22B are views showing an essential structure of the polishing apparatus having the eddy current sensor, FIG. 22A being a view showing an entire structure of the polishing apparatus including a control unit of the eddy current sensor, and FIG. 22B being an enlarged cross-sectional view of an eddy current sensor section.
Figure 22B:
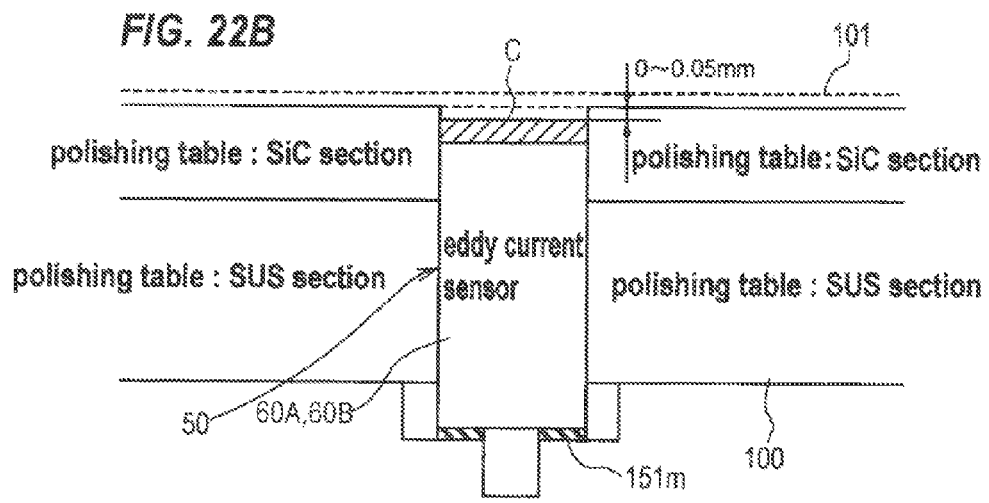

FIGS. 22A and 22B are views showing an essential structure of the polishing apparatus having the eddy current sensor 50. FIG. 22A is a view showing an entire structure of the polishing apparatus including a control unit of the eddy current sensor 50, and FIG. 22B is an enlarged cross-sectional view of an eddy current sensor section. As shown in FIG. 22A, the polishing table 100 is rotatable about its own axis as indicated by the arrow. The sensor coils 60A, 60B each having an integrated preamplifier including the AC signal source and the synchronous detection circuit are embedded in the polishing table 100. A connection cable of each of the sensor coils 60A, 60B extends through the table shaft 100a and a rotary joint 150 mounted on a shaft end of the table shaft 100a, and each of the sensor coils 60A, 60B is connected to a controller 56 through a main amplifier 55 by the connection cable. The sensor coils 60A, 60B may be provided with the main amplifier 55 integrally.

The controller 56 has a various type of filters for removing noise components from the sensor signal. These various types of filters have their respective cutoff frequencies. For example, a low-pass filter has a cutoff frequency in the range of 0.1 to 10 Hz to remove noise components which have been mixed into the sensor signal while the semiconductor wafer is being polished. Thus, the metal film (or conductive film) to be measured can be measured with high accuracy.

As shown in FIG. 22B, a polishing-pad-side end of the eddy current sensor 50 embedded in the polishing table 100 has a coating C made of a fluorine-based resin such as tetrafluoroethylene for preventing the eddy current sensor from being removed from the polishing table when the polishing pad is removed from the polishing table. The polishing-pad-side end of the eddy current sensor is provided at a position where the upper end of the eddy current sensor is lower than an upper surface (surface facing the polishing pad) of the polishing table made of SiC or the like by a distance ranging from 0 to 0.05 mm, so that the eddy current sensor is prevented from contacting the wafer during polishing. The difference in position between the upper surface of the polishing table and the upper end of the eddy current sensor should be as small as possible. In the actual apparatus, the difference in position is generally set to about 0.02 mm. The position of the eddy current sensor is adjusted by an adjustment mechanism such as a shim (thin plate) 151m or a screw.

The rotary joint 150 serves to interconnect the sensor coils 60A, 60B and the controller 56. The rotary joint 150 can transmit signals through its rotating section, but has a limitation in the number of signal lines for transmitting the signals. Thus, the signal lines to be connected to the rotary joint are limited to eight signal lines, which are a DC voltage source line, an output signal line, and transmission lines for various types of control signals. Each of the sensor coils 60A, 60B has its oscillation frequency switchable from 2 MHz to 32 MHz, and the gain of the preamplifier is also switchable according to the type of film to be polished.

Next, a method of detecting and monitoring a metal film (or conductive film) on the semiconductor wafer during polishing in the polishing apparatus having the eddy current sensor constructed as shown in FIGS. 1 through 22 will be described below in detail.

As described in FIGS. 20A, 20B, 20C and 21, the two sensor coils 60A, 60B are connected to the respective sensor circuits. The sensor coil 60A and the sensor circuit for the sensor coil 60A integrally constitute one sensor, and the sensor coil 60B and the sensor circuit for the sensor coil 60B integrally constitute one sensor. Hereinafter, the sensor which comprises the sensor coil 60A and its sensor circuit is referred to as a sensor having a small sensor diameter, and the sensor which comprises the sensor coil 60B and its sensor circuit is referred to as a sensor having a large sensor diameter, and both sensors will be distinguished from each other.

The sensor having a small sensor diameter is referred to as a sensor which has a small outer coil diameter (D1) as shown in FIGS. 4B, 4C and 14, or has a small median coil diameter (Dc1) as shown in FIGS. 16A and 16B. The sensor having a large sensor diameter is referred to as a sensor which has a large outer coil diameter (D2) as shown in FIGS.

4B, 4C and 14, or has a large median coil diameter (Dc2) as shown in FIGS. 16A and 16B. The actual sizes of the sensor having a small sensor diameter and the sensor having a large sensor diameter, are defined in connection with the sizes of the pressure chambers of the polishing head (top ring). Therefore, these sizes will be described after describing the structure of the pressure chambers of the polishing head.

Next, the case where the output frequency of the large exciting coil in the sensor having a large sensor diameter and the output frequency of the small exciting coil in the sensor having a small sensor diameter are the same, and the case where these output frequencies are different, will be described.

In the case where the output frequencies of the large exciting coil and the small exciting coil are the same, the large detection coil in the sensor having a large sensor diameter and the small detection coil in the sensor having a small sensor diameter detect the eddy currents which have the same frequency, although the frequency range which can be detected by each of the large detection coil and the small detection coil varies.

In the case where the output frequencies of the large exciting coil and the small exciting coil are different from each other, the large detection coil in the sensor having a large sensor diameter and the small detection coil in the sensor having a small sensor diameter can detect the eddy currents which have different frequencies, by providing a certain filter respectively at each side of the detection coils.

FIG. 23A shows the relationship between a locus described when the eddy current sensor 50 scans a surface (surface to be polished) of the semiconductor wafer W and outputs of the eddy current sensor 50. As shown in FIG. 23A, while the eddy current sensor 50 passes through under the semiconductor wafer W by rotation of the polishing table 100, the sensor having a small sensor diameter and the sensor having a large sensor diameter in the eddy current sensor 50 output respective certain voltage values (V) in response to a metal film (or conductive film) mf of the semiconductor wafer W. Since the sensor having a small sensor diameter and the sensor having a large sensor diameter produce outputs in response to the metal film on the same locus, the sensor outputs can be compared with each other.

FIG. 23B is a view showing outputs of the eddy current sensor 50 when the polishing of the semiconductor wafer W is started. In FIG. 23B, the horizontal axis represents polishing time (t), and the vertical axis represents an output value (voltage value) (V) of the eddy current sensor 50 or an output value corresponding to the thickness of the metal film. The output of the sensor having a small sensor diameter is drawn with a thin solid line, and the output of the sensor having a large sensor diameter is drawn with a thick solid line. As shown in FIG. 23B, both of the sensor having a small sensor diameter and the sensor having a large sensor diameter in the eddy current sensor 50 generate outputs (voltage values) in the form of substantially rectangular pulse in response to a metal film (or conductive film) mf on the semiconductor wafer W. With respect to the output at a rising edge when the electric potential is transited from Low level to High level and the output at a falling edge when the electric potential is transited from High level to Low level, the output of the sensor having a small sensor diameter is more precipitous than that of the sensor having a large sensor diameter. It means that when the remaining film at the edge of the semiconductor wafer W is detected, the sensor having a small sensor diameter has higher resolution and higher sensitivity with respect to the diametrical direction of the wafer than the sensor having a large sensor diameter.

FIG. 23C is a view showing outputs of the eddy current sensor 50 after an elapse of a predetermined time from the start of polishing the semiconductor wafer W. In FIG. 23C, the horizontal axis represents polishing time (t), and the vertical axis represents an output value (voltage value) (V) of the eddy current sensor 50 or an output value corresponding to the thickness of the metal film. The output of the sensor having a small sensor diameter is drawn with a thin solid line, and the output of the sensor having a large sensor diameter is drawn with a thick solid line. As shown in the lower part of FIG. 23C, the metal film (or conductive film) on the semiconductor wafer has a concentric thicker portion and a concentric thinner portion. The sensor having a small sensor diameter responds more sensitively to the thickness of the metal film (or conductive film) on the semiconductor wafer W than the sensor having a large sensor diameter. Therefore, the sensor having a small sensor diameter is suitable for detecting the detailed distribution of the remaining film on the surface to be polished of the semiconductor wafer (substrate) W, and for detecting a thin film on the edge area of the semiconductor wafer W. During the polishing, the difference between the profiles (for example, difference between the target profile and the detected profile during polishing) is monitored simultaneously by the sensor having a small sensor diameter, and when the occurrence of the profile abnormality is monitored continuously, the alarm is output. On the other hand, the sensor having a large sensor diameter can detect accurately the remaining film on the whole surface, being polished, of the semiconductor wafer, therefore the sensor having a large sensor diameter is suitable for detecting the polishing end point stably.

FIG. 24 is a view showing the relationship between a polishing process from starting polishing of the semiconductor wafer to clearing (removing) of a metal film (or conductive film) mf on the central part of the semiconductor wafer and outputs of the eddy current sensor 50. As shown in FIG. 24, because the metal film (or conductive film) mf is thick at the start of polishing of the semiconductor wafer W, both outputs of the sensor having a small sensor diameter (small diameter sensor) and the sensor having a large sensor diameter (large diameter sensor) of the eddy current sensor 50 become high. Then, with progress of polishing, the metal film mf becomes thinner and both outputs of the sensor having a small sensor diameter and the sensor having a large sensor diameter of the eddy current sensor 50 become lower. During this time, the sensor having a large sensor diameter does not respond to small irregularities generated on the semiconductor wafer W during polishing as indicated by the dotted-line dl. Therefore, the sensor having a large sensor diameter is not influenced by unnecessary irregularities at the end point detection. On the other hand, the sensor having a small sensor diameter responds to the small irregularities generated on the semiconductor wafer W, and outputs small peaks. Therefore, when the state of the metal film being cleared at the central part of the wafer and the remaining metal film being present at the peripheral part of the wafer occurs, the sensor having a large sensor diameter becomes the state of no sensor sensitivity and detects the polishing end point. At this time, the sensor having a small sensor diameter has outputs only at the peripheral part of the wafer. The optimum condition for detecting the polishing end point can be selected by switching the frequency or by varying electric current which is supplied to the exciting coil.

Figure 25:
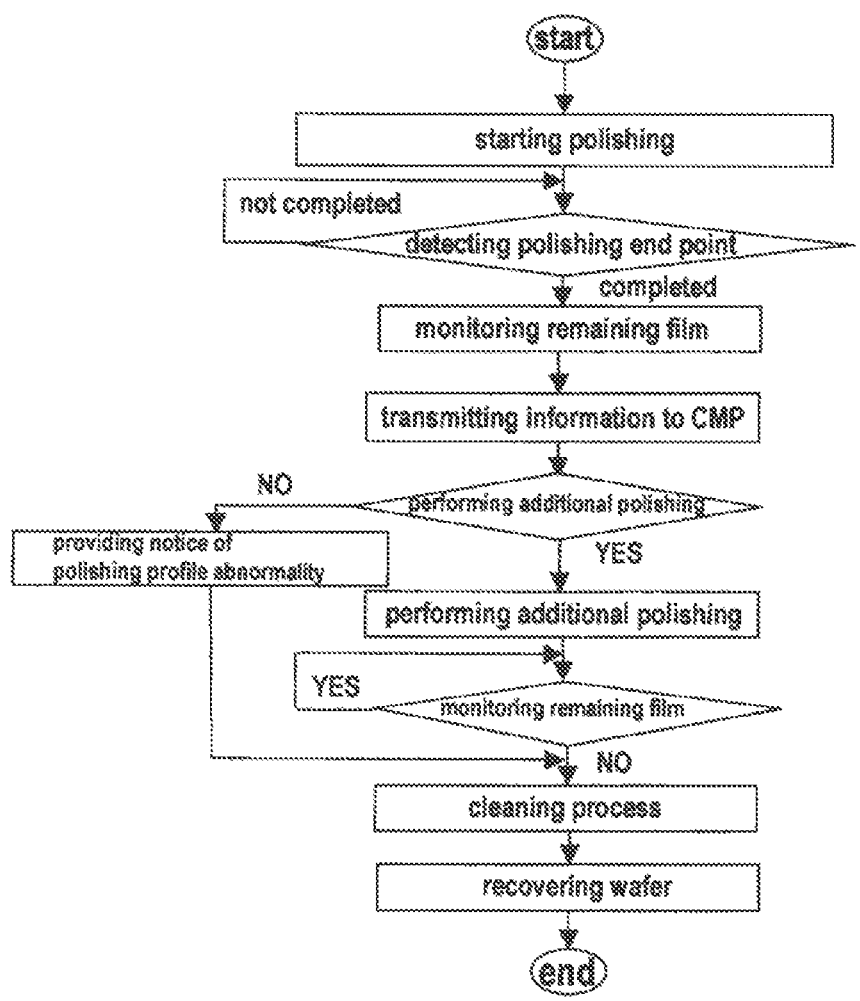
FIG. 25 is a flow chart showing procedure of polishing process and monitoring process of the metal film (or conductive film) on the semiconductor wafer.

FIG. 25 is a flow chart showing procedure of polishing process and monitoring process of the metal film (or conductive film) on the semiconductor wafer W.

As shown in FIG. 25, in the polishing apparatus, a semiconductor wafer W is taken out from a wafer cassette and transferred to the top ring 1, and the semiconductor wafer W is pressed against the polishing surface 101a on the polishing table 100 by the top ring 1, thereby starting polishing of the semiconductor wafer W. After polishing is started, the controller 56 monitors the output values of the sensor having a small sensor diameter and the sensor having a large sensor diameter of the eddy current sensor 50, and continues polishing until detection of a polishing end point and continues a monitoring process of the output values of the sensor having a small sensor diameter and the sensor having a large sensor diameter in the eddy current sensor 50. The detection of the polishing end point is conducted by detecting that the output value of the sensor having a large sensor diameter becomes the clear level of the metal film. After the polishing end point is detected, the process is shifted to monitoring of the remaining film without separating the semiconductor wafer W from the polishing surface (polishing pad). The monitoring of the remaining film is conducted by monitoring whether the sensor having a small sensor diameter has an output or not. Although FIG. 24 shows the case where the remaining film is present at the peripheral part of the wafer, if the remaining film is present locally (such as the central part of the wafer, the intermediate part of the wafer, or the like), the sensor having a small sensor diameter detects such remaining film and outputs.

Next, information obtained by monitoring of the remaining film is transmitted to the controller (process controller (not shown)) for controlling the entire CMP process. The controller (process controller) for controlling the entire CMP process may comprise a single controller including the above controller 56 or a controller different from the controller 56. The controller (process controller) judges whether or not additional polishing is necessary on the basis of the information of monitoring of the remaining film. If it is judged that the additional polishing is necessary, the additional polishing is performed, and the monitoring of the remaining film is performed. Then, after it is confirmed that there is no remaining film, the process is shifted to a cleaning process. On the other hand, if it is judged that the CMP process has some trouble, the additional polishing is not performed, but a notice of polishing profile abnormality is provided, and then the process is shifted to the cleaning process. The cleaning process is performed such that after the polished semiconductor wafer is removed from the top ring 1, scrubbing cleaning, deionized water cleaning, drying and the like are carried out by a cleaning machine in the polishing apparatus. After the cleaning process is terminated, the polished semiconductor wafer W is recovered into the wafer cassette.

Next, the monitoring of the remaining film and the additional polishing in the flow chart shown in FIG. 25 will be further described.

The monitoring of the remaining film is performed during water-polishing or overpolishing after the substantial polishing process of the wafer. Here, the water-polishing is defined as "polishing is performed by small surface pressure applied to the wafer while supplying deionized water (water) to the polishing surface." Further, the overpolishing is defined as "after detecting a characteristic point, polishing is performed for a certain period of time while a slurry is supplied to the polishing surface."

Further, in the case of detecting the remaining film by the monitoring of the remaining film, the additional polishing is performed in the following manner.

As a means for performing the additional polishing, in the case where the remaining film is detected during overpolishing, the polishing time of the overpolishing is changed. Further, in the case where the remaining film is detected at a specific location on the wafer by the monitoring of the remaining film, the additional polishing is performed by changing pressure of the top ring at the detected specific location, or the additional polishing is performed under a dedicated polishing condition. The additional polishing condition is fed back to a polishing condition for polishing a subsequent semiconductor wafer and thereafter.

In the case where the remaining film is detected by the monitoring of the remaining film, usually, the additional polishing is performed to remove the thin metal film. However, even if the planarity of the wafer is kept by the additional polishing, the CMP process may have an abnormality. Therefore, a notice of polishing profile abnormality may be provided to the controller of the polishing apparatus.

Next, the above described polishing end point detection and remaining film monitoring methods will be described as compared to the conventional method.

In the case where only a sensor (sensor A) having a certain sensitivity is used from the start of polishing until clearing of a target metal film, it is difficult to detect the metal film if the target metal film becomes thin or a remaining area of the target metal film becomes small. On the other hand, in the case where detection of a polishing end point is performed using only a sensor for thin film (sensor B), if an initial metal film is thick, outputs become over-range (out of measurement range), and thus the polishing process cannot be monitored. Therefore, in the related art, the two sensors A and B having different sensitivity are used, and outputs of the sensor A are monitored from the start of polishing until the sensor A has no sensitivity, and then detection of a polishing end point is performed. Thereafter, the sensor is switched from the sensor A to the sensor B. The remaining film monitoring is conducted by the sensor B and it is confirmed that there is no remaining metal film on the wafer.

In contrast thereto, in the case where the eddy current sensor 50 of the present invention comprising the sensor having a small sensor diameter and the sensor having a large sensor diameter as an integral unit is used, as shown in FIG. 24, because the metal film (or conductive film) mf is thick at the start of polishing of the semiconductor wafer W, an output of the sensor having a large sensor diameter becomes high. Then, with progress of polishing, the metal film mf becomes thinner and the output of the sensor having a large sensor diameter becomes lower. Then, when the state of "the metal film being cleared at the central part of the wafer/the remaining metal film being present at the peripheral part of the wafer" occurs, the sensor having a large sensor diameter becomes the state of no sensor sensitivity. Therefore, the sensor having a large sensor diameter performs detection of the polishing end point. At this time, because the sensor having a small sensor diameter has higher resolution and higher sensitivity with respect to the diametrical direction of the wafer than the sensor having a large sensor diameter, the output value at the peripheral side of the wafer becomes large in the form of a mountain, and thus the sensor having a small sensor diameter can detect the state of "the metal film being cleared at the central part of the wafer/the remaining metal film being present at the peripheral part of the wafer." Therefore, the generation of the local remaining film having a small area on the wafer can be detected by monitoring the output values of the sensor having a small sensor diameter.

Figure 26A:
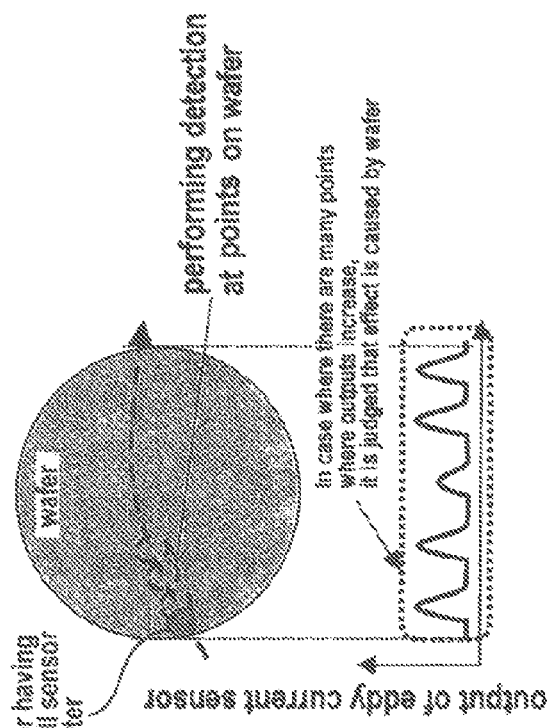
FIG. 26A is a view showing an effect of metal interconnections or the like located at the lower layer of the wafer in the case of detecting generation of the local remaining film by monitoring output values obtained by a sensor having a small sensor diameter in the eddy current sensor.
Figure 26B:
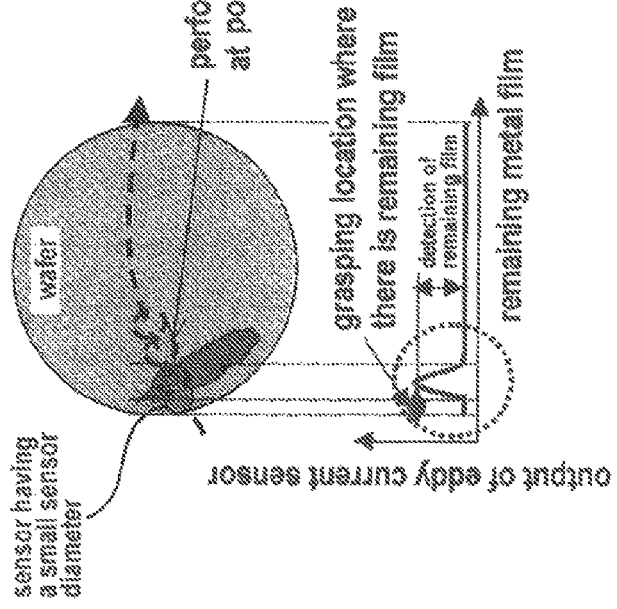
FIG. 26B is a view showing an effect of metal interconnections or the like located at the lower layer of the wafer in the case of detecting generation of the local remaining film by monitoring output values obtained by a sensor having a small sensor diameter in the eddy current sensor.

FIGS. 26A and 26B are views showing an effect of metal interconnections or the like located at the lower layer of the wafer in the case of detecting generation of the local remaining film by monitoring output values obtained by the sensor having a small sensor diameter in the eddy current sensor 50. FIG. 26A shows the case in which there is no effect of the lower layer of the wafer, and FIG. 26B shows the case in which there is an effect of the metal interconnections or the like located at the lower layer of the wafer.

As described above, the generation of the local remaining film having a small area can be detected by monitoring output values at respective measuring points on the wafer by the sensor having a small sensor diameter. However, the sensor having a small sensor diameter may be affected by metal interconnections or the like located at the lower layer of the metal film, because the sensor having a small sensor diameter has high sensitivity of the sensor. Therefore, in the case where there are many points at which outputs increase as shown in FIG. 26B, it is judged that the increased outputs are affected not by the remaining film but by the lower layer of the wafer.

Next, a locus (scanning line) described when the eddy current sensor 50 scans a surface of the semiconductor wafer will be described.

In the present invention, a ratio of the rotational speeds of the top ring 1 and the polishing table 100 is adjusted such that the loci of the eddy current sensor 50 described on the semiconductor wafer W within a predetermined period of time (e.g., within a moving average time) are distributed substantially evenly over an entire circumference of the surface of the semiconductor wafer W.

Figure 27:
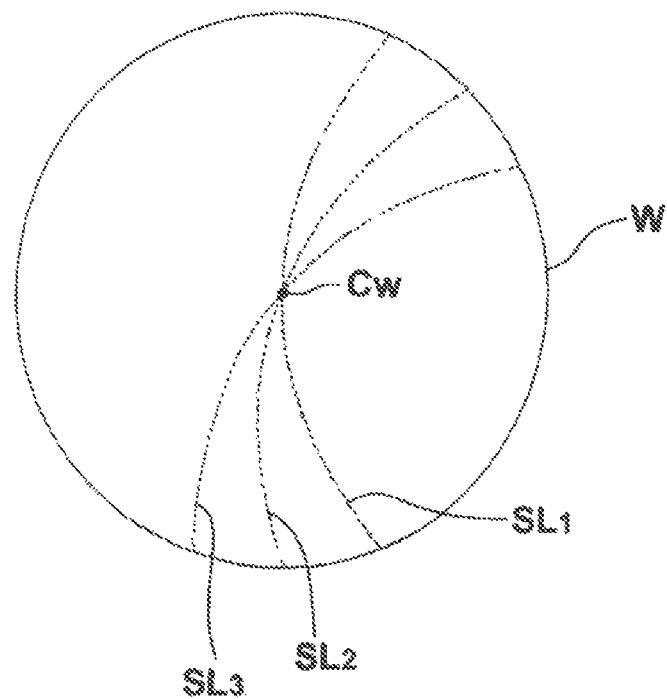
FIG. 27 is a schematic view showing loci of the eddy current sensor sweeping across the semiconductor wafer.

FIG. 27 is a schematic view showing loci of the eddy current sensor 50 sweeping across the semiconductor wafer W. As shown in FIG. 27, the eddy current sensor 50 scans the surface (surface to be polished) of the semiconductor wafer W each time the polishing table 100 makes one revolution. Specifically, when the polishing table 100 is being rotated, the eddy current sensor 50 sweeps across the surface, being polished, of the semiconductor wafer W in a locus passing through the center $C_w$ of the semiconductor wafer W (center of the top ring shaft 111). A rotational speed of the top ring 1 is set to be different from a rotational speed of the polishing table 100. Therefore, the locus of the eddy current sensor 50 described on the surface of the semiconductor wafer W changes as the polishing table 100 rotates, as indicated by scanning lines $SL_1$, $SL_2$, $SL_3$, . . . in FIG. 27. Even in this case, since the eddy current sensor 50 is located so as to pass through the center $C_w$ of the semiconductor wafer W as described above, the locus of the eddy current sensor 50 passes through the center $C_w$ of the semiconductor wafer W in every rotation.

Figure 28:
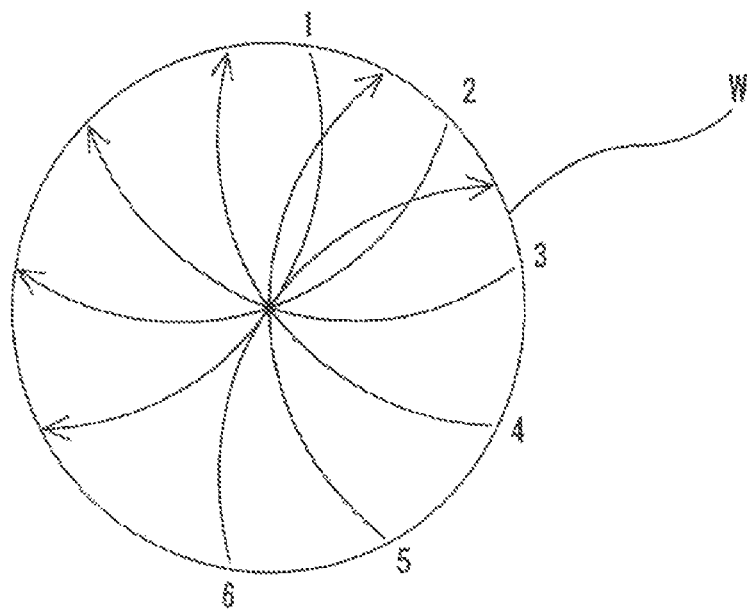
FIG. 28 is a schematic view showing loci of the eddy current sensor sweeping across the semiconductor wafer.

FIG. 28 is a view showing the loci of the eddy current sensor 50 described on the semiconductor wafer within the moving average time (5 seconds in this example) in the case where the rotational speed of the polishing table 100 is 70 $\min^{-1}$ and the rotational speed of the top ring 1 is 77 $\min^{-1}$. As shown in FIG. 28, under these conditions, the locus of the eddy current sensor 50 rotates by 36 degrees each time the polishing table 100 makes one revolution. Therefore, the locus of the eddy current sensor 50 rotates by half of the circumference of the semiconductor wafer W every time the eddy current sensor 50 scans five times. In view of a curvature of the sensor locus, six-time sweep motions of the eddy current sensor 50 across the semiconductor wafer W within the moving average time allow the eddy current sensor 50 to scan the entire surface of the semiconductor wafer W substantially evenly.

While the rotational speed of the top ring 1 is higher than the rotational speed of the polishing table 100 in the above-described example, the rotational speed of the top ring 1 may be lower than the rotational speed of the polishing table 100 (for example, the rotational speed of the polishing table 100 may be set to 70 $\min^{-1}$ and the rotational speed of the top ring 1 may be set to 63 $\min^{-1}$). In this case, the sensor locus rotates in the opposite direction, but the loci of the eddy current sensor 50 described on the surface of the semiconductor wafer W within the predetermined period of time are distributed over the entire circumference of the surface of the semiconductor wafer W as well as the above example.

Further, while the ratio of the rotational speeds of the top ring 1 and the polishing table 100 is close to 1 in the above-described example, the ratio of the rotational speeds may be close to 0.5, 1.5, or 2 (i.e., a multiple of 0.5). In this case also, the same results can be obtained. For example, when the ratio of the rotational speeds of the top ring 1 and the polishing table 100 is set to 0.5, the sensor locus rotates by 180 degrees each time the polishing table 100 makes one revolution. When viewed from the semiconductor wafer W, the eddy current sensor 50 moves along the same locus in the opposite direction each time the polishing table 100 makes one revolution.

The ratio of the rotational speeds of the top ring 1 and the polishing table 100 may be slightly shifted from 0.5 (for example, the rotational speed of the top ring 1 may be set to 36 $\min^{-1}$ and the rotational speed of the polishing table 100 may be set to 70 $\min^{-1}$), so that the sensor locus rotates by 180+α degrees each time the polishing table 100 makes one revolution. In this case, the sensor locus is shifted by an apparent angle of α degree(s). Therefore, it is possible to establish the value of α (i.e., the ratio of the rotational speeds of the top ring 1 and the polishing table 100) such that the sensor locus rotates about 0.5 time, or about N time(s), or about 0.5+N times (in other words, a multiple of 0.5, i.e., 0.5×N time(s) (N is a natural number)) on the surface of the semiconductor wafer W within the moving average time.

This method of distributing the loci of the eddy current sensor 50 on the surface of the semiconductor wafer W substantially evenly over the entire circumference of the semiconductor wafer W within the moving average time can allow wide selection of the ratio of the rotational speeds, in consideration of the adjustment of the moving average time. Therefore, this method can be applied to a polishing process which requires great variation of the ratio of the rotational speeds of the top ring 1 and the polishing table 100 in accordance with polishing conditions such as characteristics of a polishing liquid (slurry).

Figure 29:
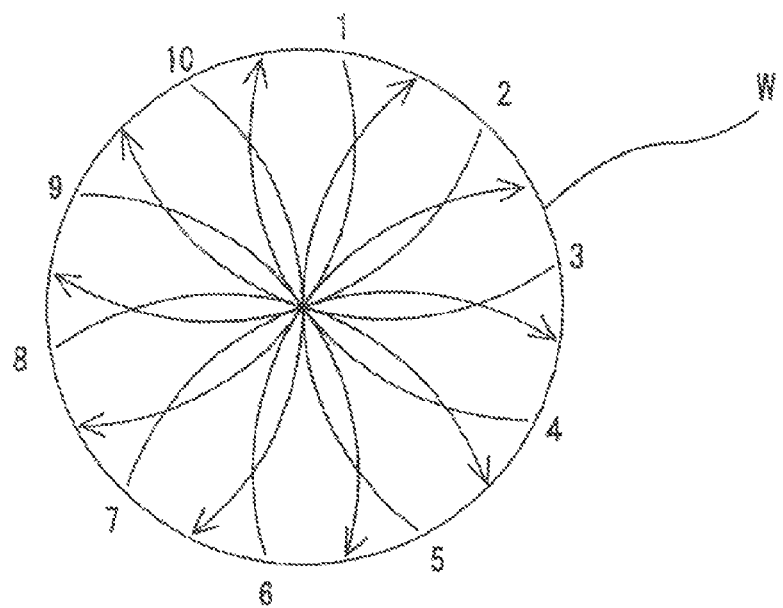
FIG. 29 is a schematic view showing loci of the eddy current sensor sweeping across the semiconductor wafer.

Generally, the locus of the eddy current sensor 50 described on the semiconductor wafer W is curved as shown in FIG. 25, except in a case where the rotational speed of the top ring 1 is just half the rotational speed of the polishing table 100. Therefore, even when the loci of the eddy current sensor 50 on the surface of the semiconductor wafer W are distributed over the entire circumference of the semiconductor wafer W within a predetermined time (e.g., the moving average time), these sensor loci are not evenly distributed in the circumferential direction of the semiconductor wafer W in a strict sense. To exactly distribute the sensor loci evenly in the circumferential direction of the semiconductor wafer W, it is necessary that the sensor locus rotates just N time(s) (N is a natural number) on the semiconductor wafer W in every predetermined period of time. During this period of time, the eddy current sensor 50 scans the surface of the semiconductor wafer W in directions or orientations that are distributed evenly in the circumferential direction of the semiconductor wafer W over the entire circumference thereof. To realize this, the rotational speeds of the polishing table 100 and the top ring 1 are determined such that, while the polishing table 100 makes a predetermined number (natural number) of revolutions, the top ring 1 makes just a predetermined number (natural number) of revolutions that is different from the predetermined number of revolutions of the polishing table 100. In this case also, since the sensor loci are curved as described above, it cannot be said that these loci are distributed at equal intervals in the circumferential direction. However, supposing that every two sensor loci make one pair, the sensor loci can be regarded as being distributed evenly in the circumferential direction at an arbitrary radial position. FIG. 29 shows this example. Specifically, FIG. 29 is a view showing the sensor loci on the semiconductor wafer W while the polishing table 100 makes ten revolutions under the same conditions as those in FIG. 28. As can be understood from the above description, the eddy current sensor 50 can obtain data that more evenly reflect various structures of the entire surface of the semiconductor wafer W, compared with the above example.

Figure 30:
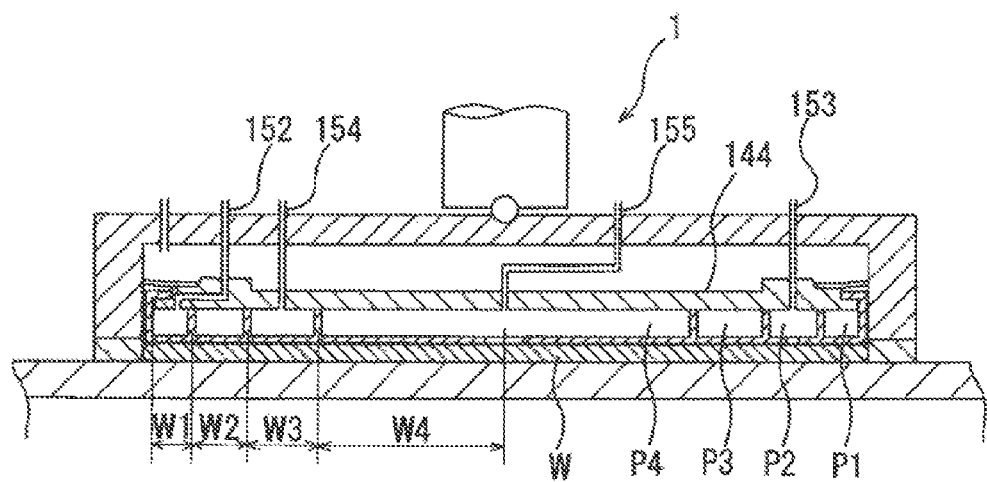
FIG. 30 is a schematic cross-sectional view showing a top ring having a plurality of pressure chambers which is suitably used in the polishing apparatus according to the present invention.

FIG. 30 is a schematic cross-sectional view showing a top ring having a plurality of pressure chambers which is suitably used in the polishing apparatus according to the present invention. The top ring 1 has a circular elastic pad 142 which is brought into contact with the semiconductor wafer W, and a chucking plate 144 for holding the elastic pad 142. An upper circumferential end portion of the elastic pad 142 is held by the chucking plate 144, and four pressure chambers (air bags) P1, P2, P3 and P4 are provided between the elastic pad 142 and the chucking plate 144. The pressure chambers P1, P2, P3 and P4 are supplied with a pressurized fluid such as pressurized air through respective fluid passages 152, 153, 154 and 155 or are vacuumed through the respective fluid passages 152, 153, 154 and 155. The central pressure chamber P4 is circular, and the other pressure chambers P3, P2 and P1 are annular. These pressure chambers P1, P2, P3 and P4 are arranged in a concentric fashion.

Internal pressures of the pressure chambers P1, P2, P3 and P4 are independently variable by pressure regulating units (not shown). Thus, pressing forces for pressing a semiconductor wafer W against the polishing pad can be independently adjusted at four areas of the semiconductor wafer W, i.e. an outer circumferential edge area, an outer intermediate area, an inner intermediate area, and a central area of the semiconductor wafer W. In this embodiment, the pressure chambers P1, P2, P3 and P4 constitute pressing mechanisms for pressing the four areas of the semiconductor wafer W independently. A thickness of the metal film (or conductive film) mf of the semiconductor wafer W is measured by the eddy current sensor 50 (see FIG. 1) provided in the polishing table 100 during polishing, and a thickness distribution of the film in a radial direction of the semiconductor wafer W is acquired by the controller 56 (see FIG. 22). The controller 56 controls internal pressures of the pressure chambers P1, P2, P3 and P4 in accordance with the thickness distribution of the film. For example, in the case where the metal film (or conductive film) mf on the semiconductor wafer W is thicker at the outer circumferential edge portion of the metal film (or conductive film) mf than at the central portion of the metal film (or conductive film) mf, the pressure of the pressure chamber P1 is made higher than the pressure of the pressure chamber P4 to allow polishing pressure of the outer circumferential edge portion of the metal film (or conductive film) to be higher than polishing pressure of the central portion of the metal film (or conductive film), thereby achieving a desired polishing profile.

The configuration of the eddy current sensor 50 and the data processing method in the case where the metal film (or conductive film) on the semiconductor wafer W is monitored in the polishing apparatus which comprises the top ring 1 having the pressure chambers P1 to P4 as shown in FIG. 30 and the polishing table 100 having the eddy current sensor 50 embedded therein will be described.

In the present invention, the internal pressures of the pressure chambers P1, P2, P3 and P4 are controlled in accordance with the thickness distribution of the film, and the film thicknesses beneath the respective pressure chambers are controlled. The widths in a radial direction of the pressure chambers P1, P2, P3 and P4 which are concentrically provided are determined to have the relation W1<W2<W3<W4 when the width of the pressure chamber P1 is W1, the width of the pressure chamber P2 is W2, the width of the pressure chamber P3 is W3, and the width of the pressure chamber P4 is W4. The sensor diameter of the sensor having a small sensor diameter is determined so that it can detect an area which is smaller than the width W1 of the pressure chamber P1. On the other hand, the sensor diameter of the sensor having a large sensor diameter is larger than that of the sensor having a small sensor diameter, and is determined so that even the sensor having the largest size can detect an area which is smaller than the width W4 of the largest pressure chamber P4. In the present invention, the sizes of the sensors (sensor diameters) are determined in accordance with the widths W1 to W4 in a radial direction of the pressure chambers P1 to P4, and can respond to the polishing pressures which are controlled independently with respect to the each area of the semiconductor wafer W by the pressure chambers P1 to P4. Specifically, during polishing, the film thickness of the edge area of the semiconductor wafer W is detected by the sensor having a small sensor diameter, which is smaller than the width W1 in a radial direction of the pressure chambers P1. The film thickness of the central area of the semiconductor wafer W is detected by the sensor having a sensor diameter which is smaller than the width W4 in a radial direction of the pressure chambers P4 and larger than the above-mentioned sensor having a small sensor diameter. Hence, in the present invention, the sensor having a small sensor diameter and the sensor having a large sensor diameter are provided so as to correspond to the plural pressure chambers which press the semiconductor wafer (substrate) W at respective areas independently of each other, and are configured to be able to detect the eddy currents at the respective areas of the semiconductor wafer (substrate) W, corresponding to the plural pressure chambers. Therefore, in the present invention, the eddy current generated in a small area of the edge area of the semiconductor wafer which has been difficult to detect, can be detected.

Conventionally, although attempt has been made to polish the semiconductor wafer flat, the surface, being polished, has been more likely to become concave because only the edge area has not been polished, or the surface, being polished, has been more likely to become convex because only the edge area has been polished faster. Further, monitoring of the polishing state has been difficult because it has been difficult to ensure one or more measuring points in the edge area having a narrow width. Under these circumstances, the control of polishing the edge area of the semiconductor wafer has been difficult. In contrast, according to the present invention, the accuracy of polishing can be improved by increasing the accuracy of detecting the polishing state at the narrow edge area of the semiconductor wafer.

As a method for determining the sensor diameter, the sampling interval of the eddy current sensor 50 and the rotational speed of the polishing table 100 can be used as barometers. For example, in the case where the sampling interval of the eddy current sensor 50 is 1 msec, if the rotational speed of the polishing table 100 is 150 rpm, the moving distance of the eddy current sensor 50 per 1 msec is 3 mm. Therefore, the sensor diameter of the small sensor is set to 3 mm, and the sensor diameter of the large sensor is set to be larger than 3 mm.

With respect to the data processing method, conventionally, the sampling interval of the eddy current sensor 50 has been set to process the data at the same sampling interval both in the edge area and in the central area of the semiconductor wafer W. However, in the present invention, because the area which can be monitored in the edge area of the semiconductor wafer W is widened, the sampling frequencies are set at 10 to 100 times (or not less than 100 times) larger than the conventional frequencies. Therefore, the detection accuracy can be increased and data collection can be performed efficiently.

For example, in the case where the rotational speed of the polishing table 100 is 60 rpm, the moving distance of the eddy current sensor 50 per 1 msec is about 1.2 mm. If the rotational speed of the polishing table 100 is increased, the moving distance of the eddy current sensor 50 per 1 msec becomes larger, and the eddy current sensor 50 cannot obtain data sufficiently in the edge area of the semiconductor wafer W. Therefore, in the present invention, the resolution can be increased by performing the data sampling by the eddy current sensor 50 at different sampling intervals in the edge area and in the central area of the semiconductor wafer W.

FIG. 31 is a view showing an embodiment in which the sampling interval can be changed in accordance with the widths in a radial direction of the pressure chambers P1 to P4. The left part of FIG. 31 shows the relationship between a locus described when the eddy current sensor 50 scans a surface (surface being polished) of the semiconductor wafer W and an output of the eddy current sensor 50. The right part of FIG. 31 shows the output of the eddy current sensor 50 and sampling intervals at respective pressure chambers P1 to P4.

As shown in FIG. 31, the sampling interval can be changed in accordance with the widths in a radial direction of the pressure chambers P1 to P4. The sampling interval is set to be short when the width in a radial direction of the pressure chamber is small, like the pressure chambers P1, P2. The sampling interval is set to be longer as the width in a radial direction of the pressure chamber becomes larger, like the pressure chambers P3, P4. In the embodiment shown in FIG. 31, the sampling intervals are set to 10 μ sec at the pressure chambers P1, P2, 100 μ sec at the pressure chamber P3, and 1 msec at the pressure chamber P4. As described above, the sampling frequencies in the present invention are set at 10 to 100 times (or not less than 100 times) larger than the conventional frequencies, and the detection accuracy can be increased and data collection can be performed efficiently.

Although certain preferred embodiments of the present invention have been shown and described in detail, it should be understood that various changes and modifications may be made therein without departing from the scope of the appended claims.

What is claimed is:

1. An eddy current sensor disposed near a metal film or a conductive film formed on a substrate to detect an eddy current generated in the metal film or the conductive film, said eddy current sensor comprising:
   a plurality of detection coils comprising an inner detection coil and an outer detection coil spaced from each other, said outer detection coil being configured to surround said inner detection coil; and
   a plurality of exciting coils comprising an inner exciting coil and an outer exciting coil spaced from each other, said outer exciting coil being configured to surround said inner exciting coil;
   wherein said plurality of detection coils are configured to detect respective eddy currents generated in the metal film or the conductive film; and
   wherein each of said plurality of exciting coils is connected to an AC signal source and configured to generate an eddy current in the metal film or the conductive film.

2. An eddy current sensor according to claim 1, further comprising:
   a plurality of dummy coils connected to the respective detection coils in series,
   wherein said plurality of dummy coils comprise an inner dummy coil and an outer dummy coil spaced from each other, said outer dummy coil being configured to surround said inner dummy coil.

3. An eddy current sensor according to claim 2, wherein at least one of said plurality of dummy coils comprises a coil formed by winding a wire or a conductive material by a single row and plural layers, said row being defined as a direction perpendicular to the substrate and said layer being defined as a direction parallel to the substrate.

4. An eddy current sensor according to claim 2, wherein at least one type of coils among said detection coils, said exciting coils and said dummy coils comprises a plurality of coils connected in series to each other, each coil being formed by winding a wire or a conductive material by a single row and plural layers, said row being defined as a direction perpendicular to the substrate and said layer being defined as a direction parallel to the substrate.

5. An eddy current sensor according to claim 2, wherein said detection coils, said exciting coils and said dummy coils are housed in a tubular member made of a material having a high-magnetic permeability.

6. An eddy current sensor according to claim 1, wherein at least one of said plurality of detection coils comprises a coil formed by winding a wire or a conductive material by a single row and plural layers, said row being defined as a direction perpendicular to the substrate and said layer being defined as a direction parallel to the substrate.

7. An eddy current sensor according to claim 1, wherein at least one of said plurality of exciting coils comprises a coil formed by winding a wire or a conductive material by a single row and plural layers, said row being defined as a direction perpendicular to the substrate and said layer being defined as a direction parallel to the substrate.

8. An eddy current sensor according to claim 1, wherein said exciting coil is curved so as to be closer to the substrate toward a radially outward edge of said exciting coil.

9. An eddy current sensor disposed near a metal film or a conductive film formed on a substrate to detect an eddy current generated in the metal film or the conductive film, said eddy current sensor comprising:
   a plurality of detection coils arranged one above the other in a direction perpendicular to the substrate, said plurality of detection coils having different sizes formed by winding a wire or a conductive material,
wherein said plurality of detection coils are configured to detect respective eddy currents generated in the metal film or the conductive film; and
a plurality of exciting coils, each of said plurality of exciting coils being connected to an AC signal source and configured to generate an eddy current in the metal film or the conductive film,
wherein said plurality of exciting coils are arranged one above the other in a direction perpendicular to the substrate.

10. An eddy current sensor according to claim 9, wherein said plurality of detection coils comprise a coil having a small outer coil diameter and a coil having a large outer coil diameter, or a coil having a small median coil diameter and a coil having a large median coil diameter, the median coil diameter being defined as an arithmetic average of an inner diameter and an outer diameter of the coil.

11. An eddy current sensor according to claim 10, wherein a plurality of said coils having a small outer coil diameter are connected in series to form a serially connected coils having a small outer coil diameter, and a plurality of said coils having a large outer coil diameter are connected in series to form a serially connected coils having a large outer coil diameter, and one of said serially connected coils having a small outer coil diameter and said serially connected coils having a large outer coil diameter is located between said serially connected coils of the other.

12. An eddy current sensor according to claim 10, wherein a plurality of said coils having a small median coil diameter are connected in series to form a serially connected coils having a small median coil diameter, and a plurality of said coils having a large median coil diameter are connected in series to form a serially connected coils having a large median coil diameter, and one of said serially connected coils having a small median coil diameter and said serially connected coils having a large median coil diameter is located between said serially connected coils of the other.

13. An eddy current sensor according to claim 9, further comprising:
a plurality of dummy coils connected to the respective detection coils in series,
wherein said plurality of dummy coils are arranged one above the other in a direction perpendicular to the substrate.

14. An eddy current sensor according to claim 13, wherein at least one of said plurality of dummy coils comprises a coil formed by winding a wire or a conductive material by a single row and plural layers, said row being defined as a direction perpendicular to the substrate and said layer being defined as a direction parallel to the substrate.

15. An eddy current sensor according to claim 13, wherein at least one type of coils among said detection coils, said exciting coils and said dummy coils comprises a plurality of coils connected in series to each other, each coil being formed by winding a wire or a conductive material by a single row and plural layers, said row being defined as a direction perpendicular to the substrate and said layer being defined as a direction parallel to the substrate.

16. An eddy current sensor according to claim 13, wherein said detection coils, said exciting coils and said dummy coils are housed in a tubular member made of a material having a high-magnetic permeability.

17. An eddy current sensor according to claim 9, wherein at least one of said plurality of detection coils comprises a coil formed by winding the wire or the conductive material by a single row and plural layers, said row being defined as a direction perpendicular to the substrate and said layer being defined as a direction parallel to the substrate.

18. An eddy current sensor according to claim 9, wherein at least one of said plurality of exciting coils comprises a coil formed by winding a wire or a conductive material by a single row and plural layers, said row being defined as a direction perpendicular to the substrate and said layer being defined as a direction parallel to the substrate.

19. An eddy current sensor according to claim 9, wherein said exciting coil is curved so as to be closer to the substrate toward a radially outward edge of said exciting coil.

20. An eddy current sensor disposed near a metal film or a conductive film formed on a substrate to detect an eddy current generated in the metal film or the conductive film, said eddy current sensor comprising:
an inner sensor coil having a first detection coil and a first exciting coil; and
an outer sensor coil having a second detection coil and a second exciting coil;
wherein said first detection coil is formed by winding a wire or a conductive material by a single row and plural layers, said row being defined as a direction perpendicular to the substrate and said layer being defined as a direction parallel to the substrate, and configured to detect eddy current;
wherein said first exciting coil is formed by winding a wire or a conductive material by a single row and plural layers, said row being defined as a direction perpendicular to the substrate and said layer being defined as a direction parallel to the substrate, and configured to be connected to an AC signal source and to generate an eddy current in the metal film or the conductive film;
wherein said second detection coil is formed by winding a wire or a conductive material by a single row and plural layers, said row being defined as a direction perpendicular to the substrate and said layer being defined as a direction parallel to the substrate, and configured to detect eddy current;
wherein said second exciting coil is formed by winding a wire or a conductive material by a single row and plural layers, said row being defined as a direction perpendicular to the substrate and said layer being defined as a direction parallel to the substrate, and configured to be connected to an AC signal source and to generate an eddy current in the metal film or the conductive film; and
wherein said inner sensor coil and said outer sensor coil are spaced from each other, said outer sensor coil being configured to surround said inner sensor coil.

* * * * *